US009241898B2

(12) United States Patent
Saltzman et al.

(10) Patent No.: US 9,241,898 B2
(45) Date of Patent: Jan. 26, 2016

(54) COMPOSITIONS AND METHODS FOR CONTROLLED DELIVERY OF INHIBITORY RIBONUCLEIC ACIDS

(75) Inventors: W. Mark Saltzman, New Haven, CT (US); Kim Woodrow, Guilford, CT (US)

(73) Assignee: Yale University, New Haven, CT (US)

(*) Notice: Subject to any disclaimer, the term of this patent is extended or adjusted under 35 U.S.C. 154(b) by 264 days.

(21) Appl. No.: 12/922,023

(22) PCT Filed: Mar. 11, 2009

(86) PCT No.: PCT/US2009/036803
§ 371 (c)(1),
(2), (4) Date: Sep. 10, 2010

(87) PCT Pub. No.: WO2009/114614
PCT Pub. Date: Sep. 17, 2009

(65) Prior Publication Data
US 2011/0008451 A1   Jan. 13, 2011

Related U.S. Application Data

(60) Provisional application No. 61/074,070, filed on Jun. 19, 2008, provisional application No. 61/068,987, filed on Mar. 11, 2008.

(51) Int. Cl.
C07H 21/04   (2006.01)
C07H 21/02   (2006.01)
A61K 9/14   (2006.01)
A61K 9/00   (2006.01)
A61K 9/51   (2006.01)
C12N 15/11   (2006.01)
C12N 15/113   (2010.01)

(52) U.S. Cl.
CPC ............. *A61K 9/0034* (2013.01); *A61K 9/0014* (2013.01); *A61K 9/0036* (2013.01); *A61K 9/5146* (2013.01); *A61K 9/5153* (2013.01); *C12N 15/111* (2013.01); *C12N 15/1137* (2013.01); *C12Y 207/01037* (2013.01); *C12N 2310/14* (2013.01); *C12N 2320/32* (2013.01)

(58) Field of Classification Search
None
See application file for complete search history.

(56) References Cited

U.S. PATENT DOCUMENTS

| 3,266,987 | A | 8/1966 | Crowley | |
|---|---|---|---|---|
| 4,460,563 | A | 7/1984 | Calanchi | |
| 4,794,000 | A | 12/1988 | Ecanow | |
| 5,623,824 | A | 4/1997 | Yukawa | |
| 5,698,546 | A | 12/1997 | Bridger | |
| 6,254,890 | B1* | 7/2001 | Hirosue et al. | 424/490 |
| 6,265,389 | B1* | 7/2001 | Burke | 514/44 A |
| 6,429,200 | B1 | 8/2002 | Monahan | |
| 6,610,478 | B1 | 8/2003 | Takle | |
| 6,770,740 | B1* | 8/2004 | Rice et al. | 530/300 |
| 2002/0012652 | A1* | 1/2002 | Levy et al. | 424/85.2 |
| 2002/0081736 | A1 | 6/2002 | Conroy | |
| 2003/0026831 | A1 | 2/2003 | Lakkaraju | |
| 2003/0082103 | A1 | 5/2003 | Wartchow | |
| 2006/0002852 | A1 | 1/2006 | Saltzman | |
| 2006/0002971 | A1 | 1/2006 | Saltzman | |
| 2006/0084617 | A1 | 4/2006 | Satishchandran | |

FOREIGN PATENT DOCUMENTS

| GB | B929401 | 6/1963 |
|---|---|---|
| GB | B929406 | 6/1963 |
| WO | 9011364 | 10/1990 |
| WO | 9312096 | 6/1993 |
| WO | 9322434 | 11/1993 |
| WO | 9524489 | 9/1995 |
| WO | 9621731 | 7/1996 |
| WO | 0210142 | 2/2002 |
| WO | WO 03/087384 | * 10/2003 |
| WO | 2006023491 | 3/2006 |
| WO | 2006133099 | 12/2006 |

OTHER PUBLICATIONS

Aguado and Lambert, "Controlled-release vaccines—biodegradable olylactide/polyglycolide (PL/PG) microspheres as antigen vehicles", Immunobiology, 184 (2-3):113-25 (1992).
Atschul, et al.,"Basic local alignment search tool", J. Molec. Biol., 215:403-10 (1990).
Bachrach, "Naturally occurring polyamines: Interaction with macromolecules", Current Protein & Peptide Science, 6:559-566 (2005).
Bartel, "MicroRNAs: genomics, biogenesis, mechanism, and function",Cell, 116(2):281-97 (2004).
Bitko, et al., "Inhibition of respiratory viruses by nasally administered siRNA", Nat Med, 11: 50-55 (2005).
Braden, et al., "Polymeric nanoparticles for sustained down-regulation of annexin A2 lead to reduction in proliferation and migration of prostate cancer cells", Journal of Biomedical Nanotechnology 3:148-159 (2007).
Bramwell, et al., "Particulate delivery systems for biodefense subunit vaccines" Adv. Drug Deliv. Rev., 57(9):1247-65 (2005).

(Continued)

*Primary Examiner* — Richard Schnizer
(74) *Attorney, Agent, or Firm* — Pabst Patent Group LLP

(57) ABSTRACT

Polymeric nanoparticles encapsulating inhibitory ribonucleic acids (RNAs) and methods of their manufacture and use are provided. Advantageous properties of the nanoparticles include: 1) high encapsulation efficiency of inhibitory RNAs into the nanoparticles, 2) small size of the nanoparticles that increases cell internalization, and 3) sustained release of encapsulated inhibitory RNAs by the nanoparticles that allows for administration of an effective amount of inhibitory RNAs to cells or tissues over extended periods of time. Encapsulation efficiency of inhibitory RNAs into the nanoparticles is greatly increased by complexing the inhibitory RNAs to polycations prior to encapsulation. Methods of using the polymeric nanoparticles for treating or inhibiting diseases or disorders are provided.

22 Claims, 3 Drawing Sheets

(56) References Cited

OTHER PUBLICATIONS

Burke, et al., "The influence of adjuvant on the therapeutic efficacy of a recombinant genital herpes vaccine", J. Inf. Dis., 170:1110-19 (1994).
Carillo and Lipman, "The Multiple Sequence Alignment Problem in Biology", SIAM J. Applied Math., 48:1073-82 (1988).
Childs, et al., "Polyamine-dependent gene expression", Cellular and Molecular Life Sciences 60:1394-1406 (2003).
Cho, et al., "Receptor-mediated delivery of all trans-retinoic acid to hepatocyte using poly (L-lactic acid) nanoparticles coated with galactose-carrying polystyrene", J Control Release 77:7-15 (2001).
Chonn and Cullis, "Recent advances in liposomal drug-delivery systems", Current Opinion in Biotechnology, 6:698 (1995).
Conner and Schmid, " Regulated portals of entry into the cell", Nature 422:37-44 (2003).
Desai, et al., "The mechanism of uptake of biodegradable microparticles in Caco-2 cells is size dependent", Pharm. Res., 14:1568-73 (1997).
Devereux, et al., "A comprehensive set of sequence analysis programs for the VAX", Nucleic Acids Research, 12(1): 387 (1984).
Elamanchili, et al. "Characterization of poly(D,L-lactic-co-glycolic acid) based nanoparticulate system for enhanced delivery of antigens to dendritic cells", Vaccine, 22:, 2406-2412 (2004).
Elbashir, et al., "RNA interference is mediated by 21- and 22-nucleotide RNAs" Genes Dev., 15:188 (2001).
Eliza and Szoka, "Liposome-encapsulated doxorubicin targeted to CD44: a strategy to kill CD44-overexpressing tumor cells", Cancer Res, 61:2592-2601 (2001).
Fahmy, et al., "Surface modification of biodegradable polyesters with fatty acid conjugates for improved drug targeting", Biomaterials, 26: 5727-5736 (2005).
Felgner, "Nonviral strategies for gene therapy", Scientific American, 276:102-10 (1997).
Freiberg and Zhu, "Polymer microspheres for controlled drug release", International Journal of Pharmaceutics 282:1-18 (2004).
Garber, "Better blocker: RNA interference dazzles research community", Natl. Cancer Inst., 95(7):500-2 (2003).
Gilmore, et al., "Delivery strategies for siRNA-mediated gene silencing", Current Drug Delivery, 3(2):147-155 (2006).
Gopalan, et al., "RNase P: variations and uses", J. Biol. Chem., 277:6759-6762 (2002).
Grayson, et al., "Biophysical and structural characterization of polyethylenimine-mediated siRNA delivery in vitro", Pharmaceut Res, 23:1868-1876 (2006).
Grishok, et al., "Genes and mechanisms related to RNA interference regulate expression of the small temporal RNAs that control C. elegans developmental timing", Cell, 106(1):23-34 (2001).
Guertier-Takada and Altman, "Inactivation of gene expression using ribonuclease P and external guide sequences", Methods Enzymol., 313:442-456 (2000).
Gunawardane, et al., "A slicer-mediated mechanism for repeat-associated siRNA 5' end formation in *Drosophila*", Science, 315(5818):1587-90 (2007).
Gupta, et al., "Poly(lactide-co-glycolide) microparticles for the development of single-dose controlled-release vaccines", Adv. Drug Deliv. Rev., 32(3):225-246 (1998).
Hallahan, et al., "Integrin-mediated targeting of drug delivery to irradiated tumor Blood vessels", Cancer Cell, 3:63-74 (2003).
Hamilton and Baulcombe, "A species of small antisense RNA in posttranscriptional gene silencing in plants", Science, 286(5441):950-2 (1999).
Harrison, et al., "Optimization of gene transfer using cationic lipids in cell lines and primary human CD4+ and CD34+ hematopoietic cells", Biotechniques, 19:816 (1995).
Haseloff and Gerlach, "Simple RNA enzymes with new and highly specific endoribonuclease activities", Nature, 334:585-591 (1988).
Hofland, et al., "In vivo gene transfer by intravenous administration of stable cationic lipid/DNA complex", Pharmaceutical Research, 14:742-49 (1997).

Hood, et al. "Tumor regression by targeted gene delivery to the neovasculature", Science, 296:2404-2407 (2002).
Hope, et al., "Cationic lipids, phosphatidylethanolamine and the intracellular delivery of polymeric, nucleic acid-based drugs (review)", Molecular Membrane Biology, 15:1-14 (1998).
Huang and Li, "Liposomal gene delivery: a complex package", Nature Biotechnology, 15:620-21 (1997).
Hutvagner, et al., "A cellular function from the RNA-Interference enzyme dicer in the maturation of the let-7 small temporal RNA", Science, 293:834-838 (2001).
Jiang, et al., "Biodegradable poly(lactic-co-glycolic acid) microparticles for injectable delivery of vaccine antigens", Adv. Drug Deliv. Rev., 57(3):391-410 (2005).
Jo, et al., "Non-viral gene transfection technologies for genetic engineering of stem cells", EU J Pharm and Bio., 68(1):90-104 (2007).
Khan, A. et al., "Sustained polymeric delivery of gene silencing antisense ODNs, siRNA, DNAzymes and ribozymes: in vitro and in vivo studies", J Drug Target, 12:393-404 (2004).
Kohn, et al., "Single-step immunization using a controlled release, biodegradable polymer with sustained adjuvant activity", J. Immunol. Methods, 95(1):31-8 (1986).
Kostelny, et al., "Formation of a bispecific antibody by the use of leucine zippers", J. Immunol., 148:1547-1553 (1992).
Langer, et al al., "New advances in microsphere-based single-dose vaccines", Adv. Drug Deliv. Rev., 28(1):97-119 (1997).
Li and Huang, "In vivo gene transfer via intravenous administration of cationic lipid-protamine-DNA (LPD) complexes", The Gene, 4:891 (1997).
Lopes de Menezes, et al. "In vitro and in vivo targeting of immunoliposomal doxorubicin to human B-cell lymphoma", Cancer Res 58:3320-3330 (1998).
Luo, et al., "Controlled DNA delivery systems", Pharm Res, 16:1300-1308 (1999).
Matsumoto, et al.., "Cationized gelation delivery of a plasmid DNA expressing small interference RNA for VEGF inhibits murine squamous cell carcinoma", Cancer Science, 97(4):313-321 (2006).
McManus and Sharp, "Gene silencing in mammals by small interfering RNAs", Nature Rev. Genet., 3:737-47 (2002).
Murata, et al., "Anti-tumor effects of anti-VEGF siRNA encapsulated with PLGA microspheres in mice", J. Control. Release, 126(3):246-54 (2008).
Novina and Sharp, "The RNAi revolution", Nature, 430:161-164 (2004).
Novina, et al., "siRNA-directed inhibition of HIV-1 infection", Nat Med, 8:681-686 (2002).
Olivier, "Drug transport to brain with targeted nanoparticles", Neurorx, 2:108-119 (2005).
Palliser, et al., "An siRNA-based microbicide protects mice from lethal herpes simplex virus 2 infection", Nature 439, 89-94 (2006).
Pan, et al., "Strategy for the treatment of acute myelogenous leukemia based on folate receptor beta-targeted liposomal doxorubicin combined with receptor induction using all-trans retinoic acid", Blood, 100:594-602 (2002).
Park, et al., "Anti-HER2 immunoliposomes: enhanced efficacy attributable to targeted delivery", Clin Cancer Res, 8:1172-1181 (2002).
Peer, et al., "Systemic leukocyte-directed siRNA delivery revealing cyclin D1 as an anti-inflammatory target", Science, 319:627-630 (2008).
Peeters, et al., "Adenovirus-mediated hepatic gene transfer in mice: comparison of intravascular and biliary administration", Human Gene Therapy, 7:1693 (1996).
Plehn-Dujowich and Altman, "Effective inhibition of influenza virus production in cultured cells by external guide sequences and ribonuclease P", PNAS USA, 95:7327-7332 (1998).
Radomsky, et al., "Controlled Vaginal Delivery of Antibodies in the Mouse", Biology of Reproduction, 47:133-140 (1992).
Reinhart, et al., "MicroRNAs in plants", Genes and Dev., 16:1616-1626 (2002).
Sarver, et al, "Ribozymes as potential anti-HIV-1 therapeutic agents", Science, 247:1222-1225 (1990).

(56) References Cited

OTHER PUBLICATIONS

Schiffelers, et al., "Cancer siRNA therapy by tumor selective delivery with ligand-targeted sterically stabilized nanoparticle", Nucleic Acids Res, 32, e149 (2004).

Shen, et al., "Gene expression and mucosal immune responses after vaginal DNA immunization in mice using a controlled delivery matrix", J Control Release, 86:339-348 (2003).

Songsivilai and Lachmann, "Bispecific antibody: a tool for diagnosis and treatment of disease", Clin. Exp. Immunol., 79:315-321 (1990).

Sun, et al., "Contribution of epoxyeicosatrienoic acids to flow-induced dilation in arteries of male ER alpha knockout mice: role of aromatase", Am. J. Physiology-Regulatory Integrative and Comparative Physiology 293:R1239-R1246 (2007).

Tam, et al, "Stabilized plasmid-lipid particles for systemic gene therapy", Gene Ther., 7:1867 (2000).

Templeton, et al., "Improved DNA: liposome complexes for increased systemic delivery and gene expression", Nature Biotechnology, 15:647-52 (1997).

Tigges, et al., "Human herpes simplex virus (HSV)-specific CD8+ CTL clones recognize HSV-2-infected fibroblasts after treatment with IFN-gamma or when virion host shutoff functions are disabled", J. Immunol., 156:3901-3910 (1996).

Valenta, "The use of mucoadhesive polymers in vaginal delivery", Adv Drug Deliver Rev, 57:1692-1712 (2005).

Wartlick, et al., "Highly specific HER2-mediated cellular uptake of antibody-modified modified nanoparticles in tumour cells", J Drug Target, 12:461-471 (2004).

Worgall, et al., "Innate immune mechanisms dominate elimination of adenoviral vectors following in vivo administration", Human Gene Therapy, 8:37 (1997).

Wyatt, et al., "Antigen-releasing polymer rings and microspheres stimulate mucosal immunity in the vagina", J Control Release, 50:93-102 (1998).

Yei, et al., "Adenovirus-mediated gene transfer for cystic fibrosis: quantitative evaluation of repeated in vivo vector administration to the lung", Gene Therapy, 1:192 (1994).

Yekta, et al., "MicroRNA-directed cleavage of HOXB8 mRNA", Science, 304 (5670):594-6 (2004).

Yuan, et al., "siRNA drug delivery by biodegradable polymeric nanoparticles", J. Nanosci. Nanotechnol., 6:2821-2828 (2006).

Zhang, et al., "Engineering mucosal RNA interference in vivo", Mol Ther, 14:336-342 (2006).

Zhoa, et al., "Lipofectamine RNAiMAX: An efficient siRNA transfection reagent in human embryonic stem cells", Molecular Biotechnology, 40(1):19-26 (2008).

\* cited by examiner

COMPOSITIONS AND METHODS FOR CONTROLLED DELIVERY OF INHIBITORY RIBONUCLEIC ACIDS

CROSS-REFERENCE TO RELATED APPLICATIONS

This application claims priority to and benefit of U.S. Provisional Patent Application No. 61/068,987 filed on Mar. 11, 2008, and U.S. Provisional Patent Application No. 61/074,070 filed on Jun. 19, 2008.

GOVERNMENT SUPPORT

This application is a national phase filing under 35 U.S.C. §371 of PCT/US2009/036803 filed with the Patent Cooperation Treaty on May 11, 2009, which claims priority to and benefit of U.S. Provisional Application No. 61/068,987 filed on May 11, 2008, and U.S. Provisional Patent Application No. 61/074,070 filed on Jun. 19, 2008, the contents of each being hereby incorporated by reference in their entirety.

FIELD OF THE INVENTION

The present disclosure generally relates to the field of polymeric nanoparticulate compositions for controlled and sustained release of inhibitory ribonucleic acids and methods of making and using these compositions.

BACKGROUND OF THE INVENTION

RNA interference (RNAi) mediated by short-interfering RNA (siRNA) is an emerging tool in basic science and is poised to offer new therapeutic modalities to treat various diseases. RNAi is an evolutionarily conserved, sequence specific mechanism triggered by double stranded RNA (dsRNA) that induces degradation of complementary target single stranded mRNA and "silencing" of the corresponding translated sequences (McManus and Sharp, Nature Rev. Genet., 3:737 (2002)). RNAi functions by enzymatic cleavage of longer dsRNA strands into biologically active siRNA sequences of about 21-23 nucleotides in length (Elbashir, et al., Genes Dev., 15:188 (2001)).

Inhibitory RNAs can be used downregulate or silence the translation of a gene product of interest. For example, it can be desirable to downregulate genes associated with various diseases and disorders. Although siRNAs have surpassed expectation when used to alter gene expression in the laboratory setting, RNAi-based therapies for the clinic are still limited by the availability of efficient delivery systems (Novina and Sharp, Nature, 430:161-163 (2004); Garber, Natl. Cancer Inst., 95(7):500-2 (2003)). An effective and safe nucleic acid delivery system is required for siRNA to be therapeutically useful.

Inhibitory RNAs that are administered "naked" to most subjects can be degraded by endogenous nucleases; and may not be able to cross cell membranes to contact and silence their target gene sequences. Viral vectors are relatively efficient gene delivery systems, but suffer from a variety of safety concerns, such as potential for undesired immune responses. Furthermore, viral systems are rapidly cleared from the circulation, limiting transfection to "first-pass" organs such as the lungs, liver, and spleen. In addition, these systems induce immune responses that compromise delivery with subsequent injections. As a result, nonviral gene delivery systems are receiving increasing attention (Worgall, et al., Human Gene Therapy, 8:37 (1997); Peeters, et al., Human Gene Therapy, 7:1693 (1996); Yei, et al., Gene Therapy, 1:192 (1994); Hope, et al., Molecular Membrane Biology, 15:1 (1998)).

Plasmid DNA-cationic liposome complexes are currently the most commonly employed nonviral gene delivery vehicles (Felgner, Scientific American, 276:102 (1997); Chonn, et al., Current Opinion in Biotechnology, 6:698 (1995)). Cationic liposome complexes, however, are large, poorly defined systems that are not suited for systemic applications and can elicit considerable toxic side effects (Harrison, et al., Biotechniques, 19:816 (1995); Li, et al., The Gene, 4:891 (1997); Tam, et al, Gene Ther., 7:1867 (2000)). As large, positively charged aggregates, lipoplexes are rapidly cleared when administered in vivo, with highest expression levels observed in first-pass organs, particularly the lungs (Huang, et al., Nature Biotechnology, 15:620 (1997); Templeton, et al., Nature Biotechnology, 15:647 (1997); Hofland, et al., Pharmaceutical Research, 14:742 (1997)). Although RNA lipoplexes are easily formulated and have been used successfully in a few applications, lipoplexes suffer from toxicity, especially to the vulnerable mucosal epithelium, and do not offer the potential for controlled or sustained release. Other liposomal delivery systems include, for example, the use of reverse micelles, anionic and polymer liposomes as disclosed in, e.g., U.S. Pat. No. 6,429,200; U.S. Patent Application No. 2003/0026831; and U.S. Patent Application Nos. 2002/0081736 and 2003/0082103, respectively.

Intravaginal delivery of inhibitory RNAs, including siRNA, is especially challenging but desirable because of the susceptibility of reproductive tissues to infectious diseases, which are potentially treatable by inhibitory RNA approaches (Valenta, Adv. Drug Deliver. Rev., 57:1692-1712 (2005)). To date, vaginal instillation of siRNA using commercial liposomes in murine models has led to silencing of endogenous genes (Zhang, et al., Mol. Ther., 14(3):336-42 (2006)) in the genital tract and protected against challenge from herpes simplex virus (Palliser, et al., Nature, 439(7072):89-94 (2006)).

It is therefore an object of the invention to provide compositions that can deliver high concentrations of inhibitory RNAs to cells and tissues.

It is another object of the invention to provide compositions that can deliver inhibitory RNAs to cells and tissues in a controlled and sustained manner over a period of at least one week.

It is yet another object of the invention to provide compositions that can penetrate deep into tissues and deliver inhibitory RNAs intracellularly.

It is still a further object of the invention to provide methods for making and using these inhibitory RNA delivery compositions.

SUMMARY OF THE INVENTION

Polymeric nanoparticles encapsulating high concentrations of inhibitory ribonucleic acids and methods of their manufacture and use are provided. Exemplary inhibitory RNAs include, but are not limited to, dsRNA, siRNA, shRNA, miRNA, piRNA, RNAse external guide sequences, ribozymes, and other short catalytic RNAs. Inhibitory RNAs to be encapsulated into the nanoparticles are selected to bind to, and inhibit the expression of, specific target mRNAs. mRNA targets are selected according to the disease or disorder to be treated or inhibited. Suitable mRNAs that can be targeted include, but are not limited to, mRNAs encoded by oncogenes and mRNAs encoded by viral genes.

The encapsulation efficiency of inhibitory RNAs into the nanoparticles is greatly increased by complexing the inhibitory RNAs to polycations prior to encapsulation. Suitable polycations have at least two positive charges at physiologic pH. In some embodiments the polycation is a polyamine. Exemplary polyamines include, but are not limited to, spermine, spermidine, cadaverine and putrescine. The external surface of the polymeric nanoparticles can be modified by conjugating a coupling agent to the surface of the nanoparticle. The coupling agent is preferably present in high density on the surface of the nanoparticle. Coupling agents preferably are molecules that match the polymer phase hydrophile-lipophile balance. The coupling agents can be fatty acids, hydrophobic or amphipathic peptides, or hydrophobic polymers. Coupling agents provide substrates that facilitate the modular assembly and disassembly of functional elements to the nanoparticles. The coupling agents can be conjugated to affinity tags which allow for the modular assembly and disassembly of functional elements conjugated to complementary affinity tags. Suitable functional elements that can be associated with the nanoparticles include targeting molecules, protein transduction domains and fusogenic peptides.

The nanoparticles are generally useful for intracellular delivery of inhibitory RNAs in a controlled and sustained manner. The nanoparticulate size of the polymeric particles provides for greater internalization of the particles by cells when compared with microparticulate polymeric particles. The examples demonstrate that siRNA/polycation complexes exposed to cells in the absence of nanoparticle carriers required transfection agents to be efficiently transported into cells. The advantages of the nanoparticles include high encapsulation efficiency of inhibitory RNAs into nanoparticles provided by complexing to polycations, small size of the nanoparticles that increases cell internalization of the nanoparticles, and sustained release of encapsulated inhibitory RNAs by the nanoparticles, allows for administration of an effective amount of inhibitory RNAs to cells or tissues over extended periods of time.

Methods of using the polymeric nanoparticles for treating or inhibiting diseases or disorders are provided. The diseases and disorders to be treated include any disease or disorder in which it is desirable to reduce the expression of one or more mRNAs such as, but not limited to, cancer, diseases and disorders that result from viral infections, inflammatory and autoimmune diseases and disorders, graft rejection and graft-versus-host disease. Any mRNA known to be aberrantly expressed in the condition to be treated can be targeted by inhibitory RNAs encapsulated within the nanoparticles disclose herein.

DETAILED DESCRIPTION OF THE INVENTION

I. Definitions

Figure 1:
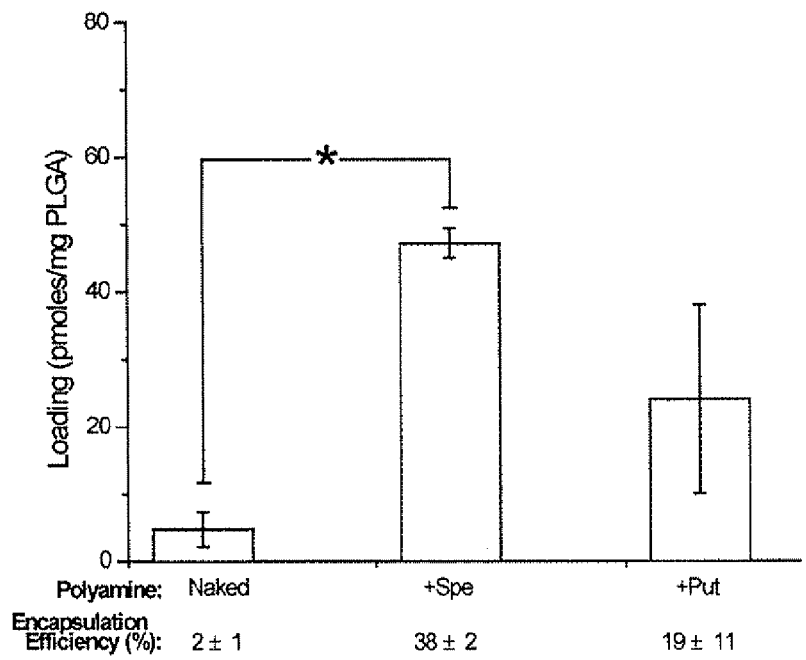
FIG. 1 is a bar graph showing the effect of natural polyamines on the actual loading (pmoles/mg PLGA) and encapsulation efficiency (%) of a siRNA mimic into PLGA nanoparticles. Naked, Spermidine (Spe) and putrescine (Put) were combined with the siRNA mimic deoMMC at a N:P ratio of 8 and then encapsulated into PLGA nanoparticles prepared by solvent evaporation from a double-emulsion. Values represent the mean±s.d. of three independent formulations; *=p≤0.05.

"Affinity tags" are defined herein as molecular species which form highly specific, non-covalent, physiochemical interactions with defined binding partners. Affinity tags which form highly specific, non-covalent, physiochemical interactions with one another are defined herein as "complementary".

"Coupling agents" are defined herein as molecular entities which associate with polymeric nanoparticles and provide substrates that facilitate the modular assembly and disassembly of functional elements onto the nanoparticle. Coupling agents can be conjugated to affinity tags. Affinity tags allow for flexible assembly and disassembly of functional elements which are conjugated to affinity tags that form highly specific, noncovalent, physiochemical interactions with affinity tags conjugated to adaptor elements. Coupling agents can also be covalently coupled to functional elements in the absence of affinity tags.

As used herein, the term "isolated" describes a compound of interest (e.g., either a polynucleotide or a polypeptide) that is in an environment different from that in which the compound naturally occurs, e.g., separated from its natural milieu such as by concentrating a peptide to a concentration at which it is not found in nature. "Isolated" is meant to include compounds that are within samples that are substantially enriched for the compound of interest and/or in which the compound of interest is partially or substantially purified.

As used herein with respect to nucleic acids, the term "isolated" includes any non-naturally-occurring nucleic acid sequence, since such non-naturally-occurring sequences are not found in nature and do not have immediately contiguous sequences in a naturally-occurring genome.

As used herein, the term "host cell" refers to prokaryotic and eukaryotic cells into which a nucleic acid can be introduced.

As used herein, "transformed" and "transfected" encompass the introduction of a nucleic acid into a cell by one of a number of techniques known in the art.

As used herein, the phrase that a molecule "specifically binds" to a target refers to a binding reaction which is determinative of the presence of the molecule in the presence of a heterogeneous population of other biologics. Thus, under designated immunoassay conditions, a specified molecule binds preferentially to a particular target and does not bind in a significant amount to other biologics present in the sample. Specific binding of an antibody to a target under such conditions requires the antibody be selected for its specificity to the target. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity. Specific binding between two entities means an affinity of at least $10^6$, $10^7$, $10^8$, $10^9$, or $10^{10}$ $M^{-1}$. Affinities greater than $10^8$ $M^{-1}$ are preferred.

As used herein, "targeting molecule" is a substance which can direct a nanoparticle to a receptor site on a selected cell or tissue type, can serve as an attachment molecule, or serve to couple or attach another molecule. As used herein, "direct" refers to causing a molecule to preferentially attach to a selected cell or tissue type. This can be used to direct cellular materials, molecules, or drugs, as discussed below.

As used herein, the terms "antibody" or "immunoglobulin" are used to include intact antibodies and binding fragments thereof. Typically, fragments compete with the intact antibody from which they were derived for specific binding to an antigen fragment including separate heavy chains, light chains Fab, Fab' F(ab')$_2$, Fabc, and Fv. Fragments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes a bispecific antibody. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai and Lachmann, Clin. Exp. Immunol., 79:315-321 (1990); Kostelny, et al., J. Immunol., 148, 1547-1553 (1992).

As used herein, the terms "epitope" or "antigenic determinant" refer to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10, amino acids, in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed. (1996). Antibodies that recognize the same epitope can be identified in a simple immunoassay showing the ability of one antibody to block the binding of another antibody to a target antigen. T-cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke, et al., J. Inf. Dis., 170:1110-19 (1994)), by antigen-dependent killing (cytotoxic T lymphocyte assay, Tigges, et al., J. Immunol., 156, 3901-3910) or by cytokine secretion.

II. Polymeric Nanoparticulate Compositions for the Delivery of Inhibitory RNAs

A. Inhibitory RNAs

The terms "inhibitory ribonucleic acid" or "inhibitory RNA" refer to RNAs specific for target RNAs that reduce of inhibit the expression of the target RNA. Inhibitory RNAs such as double-stranded RNA (dsRNA), small hairpin RNA (shRNA), small interfering RNA (siRNA), microRNA (miRNA), Piwi-interacting RNA (piRNA), ribozymes and RNAse external guide sequences (EGSs) do not integrate into the genome of cells and produce only a transient effect on levels of gene expression in a cell. Expression of the target nucleic acid can be inhibited at the transcriptional or translational level. Inhibitory RNAs can modulate target mRNA expression through several means, including directly catalyzing target mRNA degradation, causing the recruitment of cellular proteins and enzymes that mediate mRNA degradation, inhibiting or reducing the translation of target mRNA, or otherwise reducing the stability of target mRNA. The level to which gene expression is reduced in cells by inhibitory RNAs is highly dependent upon the amount of inhibitory RNA that enters the cell. Therefore, an effective inhibitory RNA delivery vehicle should be able to provide a high concentration of inhibitory RNAs in a controlled and sustained manner.

Inhibitory RNAs are configured to hybridize to target mRNAs and modulate their expression or integrity. Inhibitory RNAs are complementary to their target RNAs. The term "complementary", as used herein, refers to the capacity of two nucleotides to pair precisely with each other. This term may also be used to refer to oligonucleotides which exhibit the ability of pairing precisely with each other. For example, if the nucleotides located at a certain position on two oligonucleotides are capable of hydrogen bonding, then the oligonucleotides are considered to be complementary to each other at that position. The inhibitory RNAs and the target RNAs are complementary to each other when a sufficient number of corresponding positions in each molecule are occupied by nucleotides which can hydrogen bond with each other. Thus, "complementary" is a term that is used to indicate a sufficient degree of complementarity or precise paring such that stable and specific binding may occur between the inhibitory RNA and the target RNA. It is understood in the art that the sequence of an inhibitory oligonucleotide compound need not be 100 percent complementary to that of its target RNA. A sufficient degree of complementarity prevents non-specific binding of the inhibitory oligonucleotide compound to nontarget sequences under conditions in which specific binding is desired, i.e. under physiological conditions.

Inhibitory nucleic acids and methods of producing them are well known in the art. siRNA design software is available, for example, at http://i.cs.hku.hk/~sirna/software/sirna.php. The sequence of at least one strand of the siRNA contains a region complementary to at least a part of the target mRNA sufficient for the siRNA to specifically hybridize to the target mRNA. In one embodiment, the siRNA is substantially identical to at least a portion of the target mRNA. "Identity", as known in the art, is the relationship between two or more polynucleotide (or polypeptide) sequences, as determined by comparing the sequences. In the art, identity also means the degree of sequence relatedness between polynucleotide sequences, as determined by the match between strings of such sequences. Identity can be readily calculated (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, N.J., 1994; Sequence Analysis in Molecular Biology, von Heinje, G., Academic Press, 1987; and Sequence Analysis Primer, Gribskov, M. and Devereux, J., eds., M Stockton Press, New York, 1991). While there exist a number of methods to measure identity between two polynucleotide sequences, the term is well known to skilled artisans (Sequence Analysis in Molecular Biology, von Heinje, G., Academic Press, 1987; Sequence Analysis Primer, Gribskov, M. and Devereux, J., eds., M Stockton Press, New York, 1991; and Carillo, H., and Lipman, D., *SIAM J. Applied Math.*, 48: 1073 (1988). Methods commonly employed to determine identity between sequences include, but are not limited to those disclosed in Carillo, H., and Lipman, D., *SIAM J. Applied Math.*, 48:1073 (1988). Preferred methods to determine identity are designed to give the largest match between the sequences tested. Methods to determine identity are codified in computer programs. Computer program methods to determine identity between two sequences include, but are not limited to, GCG program package (Devereux, J., et al., *Nucleic Acids Research*, 12(1): 387 (1984)), BLASTP, BLASTN, and FASTA (Atschul, S. F. et al., *J. Molec. Biol.*, 215: 403 (1990)). Another software package well known in the art for carrying out this procedure is the CLUSTAL program. It compares the sequences of two polynucleotides and finds the optimal alignment by inserting spaces in either sequence as appropriate. The identity for an optimal alignment can also be calculated using a software package such as BLASTx. This program aligns the largest stretch of similar sequence and assigns a value to the fit. For any one pattern comparison several regions of similarity may be found, each having a different score. One skilled in the art will appreciate that two polynucleotides of different lengths may be compared over the entire length of the longer fragment. Alternatively small regions may be compared. Normally sequences of the same length are compared for a useful comparison to be made.

In one embodiment, the inhibitory nucleic acid has 100% sequence identity with at least a part of the target mRNA. However, inhibitory nucleic acids having 70%, 80% or greater than 90% or 95% sequence identity may be used. Thus sequence variations that might be expected due to genetic mutation, strain polymorphism, or evolutionary divergence can be tolerated.

The duplex region of the RNA may have a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing).

Inhibitory RNAs may contain naturally occurring bases as well as base analogs including, but not limited to, 4-acetylcytosine, 8-hydroxy-N-6-methyladenosine, aziridinylcytosine, pseudoisocytosine, 5-(carboxyhydroxylmethyl) uracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methyl guanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxy-aminomethyl-2-thiouracil, beta-D-mannosylqueosine, 5'-methoxycarbonylmethyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, 2,6-diaminopurine, and 2'-modified analogs such as, but not limited to O-methyl, amino-, and fluoro-modified analogs.

Inhibitory RNAs can be produced using methods known to those skilled in the art. They can be chemically synthesized, produced by in vitro transcription; expressed in cells from an expression plasmid or viral vector; or expressed in cells from a PCR-derived expression cassette. In vitro synthesis may be chemical or enzymatic, for example using cloned RNA polymerase (e.g., T3, T7, SP6) for transcription of the endogenous DNA (or cDNA) template, or a mixture of both. SiRNAs can also be produced by digestion of long dsRNA by an RNase III family enzyme (e.g., Dicer, RNase III). In a preferred embodiment, the inhibitory RNAs are obtained synthetically, for example, by chemically synthesizing a nucleic acid by any method of synthesis known to the skilled artisan. The synthesized inhibitory RNAs can then be purified by any method known in the art. Methods for chemical synthesis of nucleic acids include in vitro chemical synthesis using phosphotriester, phosphate or phosphoramidite chemistry and solid phase techniques, or via deoxynucleoside H-phosphonate intermediates (see, for example, U.S. Pat. No. 5,705,629 to Bhongle).

In vivo, inhibitory RNAs may be synthesized using recombinant techniques well known in the art (see, for example, Sambrook, et al., Molecular Cloning; A Laboratory Manual, Third Edition (2001)). For example, bacterial cells can be transformed with an expression vector which comprises the DNA template from which the inhibitory RNAs are to be derived. The RNA can be purified by extraction with a solvent (such as phenol/chloroform) or resin, precipitation (for example in ethanol), electrophoresis, chromatography, or a combination thereof.

Inhibitory RNAs can be designed, using principles well known in the art, to bind to, and initiate degradation of, or repress the translation of, almost any mRNA of known sequence. Inhibitory RNAs to be encapsulated in the nanoparticles can be selected to bind to and inhibit the expression of specific target mRNAs, depending on the disease or disorder to be treated or inhibited. For example, for the treatment or inhibition of cancer in a subject, inhibitory RNAs that bind to mRNA transcripts of oncogenes can be encapsulated in the nanoparticles. A large number of oncogenes are known in the art. Similarly, for the treatment or inhibition of disease or disorders caused by viral infection, inhibitory RNAs can be selected that bind to viral mRNAs that are important for the viral life-cycle or for viral cell entry. Alternatively, inhibitory RNAs can be selected that bind to endogenous cellular genes that are important for viral infection, such as cell surface receptors that mediate viral entry.

i. siRNA and shRNA

In one embodiment, the inhibitory RNAs are siRNAs or shRNAs. The term "siRNA" means a small interfering RNA that is a short-length double-stranded RNA that is not toxic. Generally, there is no particular limitation in the length of siRNA as long as it does not show toxicity. "siRNAs" can be, for example, 15 to 49 bp, preferably 15 to 35 bp, and more preferably 21 to 30 bp long.

The double-stranded RNA portions of siRNAs in which two RNA strands pair up are not limited to the completely paired ones, and may contain nonpairing portions due to mismatch (the corresponding nucleotides are not complementary) or bulge (lacking in the corresponding complementary nucleotide on one strand). Nonpairing portions can be contained to the extent that they do not interfere with siRNA formation. Suitable siRNAs can contain one or more modified bases, or have a modified a backbone to increase stability or for other reasons. For example, the phosphodiester linkages of natural RNA may be modified to include at least one of a nitrogen or a sulfur heteroatom. siRNAs comprising unusual bases, including, but not limited to, inosine, or modified bases, such as tritylated bases, can be used. The term "siRNA", as used herein, embraces chemically, enzymatically or metabolically modified forms of siRNA.

The terminal structure of siRNA may be either blunt or cohesive (overhanging) as long as siRNA can silence, reduce, or inhibit the target gene expression due to its RNAi effect. The cohesive (overhanging) end structure is not limited to the 3' overhang, and the 5' overhanging structure may be included as long as it is capable of inducing the RNAi effect. The number of overhanging nucleotide can be any numbers as long as the overhang is capable of inducing the RNAi effect. For example, the overhang can consist of 1 to 8, preferably 2 to 4, nucleotides.

The terminal structure of the siRNA is not necessarily the cut off structure at both ends as described above, and may have a stem-loop structure in which ends of one side of double-stranded RNA are connected by a linker RNA. siRNAs containing a linker RNA that forms a hairpin structure are referred to as short hairpin RNAs, or shRNAs. The length of the double-stranded RNA region (stem-loop portion) can be, for example, 15 to 49 bp, preferably 15 to 35 bp, and more preferably 21 to 30 bp long. Alternatively, the length of the double-stranded RNA region that is a final transcription product of siRNAs to be expressed is, for example, 15 to 49 bp, preferably 15 to 35 bp, and more preferably 21 to 30 bp long. There is no particular limitation in the length of the linker as long as it has a length so as not to hinder the pairing of the stem portion. For example, for stable pairing of the stem portion and suppression of the recombination between DNAs coding for the portion, the linker portion may have a cloverleaf tRNA structure. Even though the linker has a length that hinders pairing of the stem portion, it is possible, for example, to construct the linker portion to include introns so that the introns are excised during processing of precursor RNA into mature RNA, thereby allowing pairing of the stem portion.

ii. miRNA

MicroRNAs (referred to as "miRNAs") are small non-coding RNAs, belonging to a class of regulatory molecules found in plants and animals that control gene expression by binding to complementary sites on target messenger RNA (mRNA) transcripts. miRNAs are generated from large RNA precursors (termed pri-miRNAs) that are processed in the nucleus into approximately 70 nucleotide pre-miRNAs, which fold into imperfect stem-loop structures (Lee, et al., Nature, 425(6956):415-9 (2003)). The pre-miRNAs undergo an additional processing step within the cytoplasm where mature miRNAs of 18-25 nucleotides in length are excised from one side of the pre-miRNA hairpin by an RNase III enzyme, Dicer (Hutvagner, G., et al., Science, 12:12 (2001) and Grishok, et al., Cell, 106(1):23-34 (2001)). MiRNAs have been shown to regulate gene expression in two ways. First, miRNAs that bind to protein-coding mRNA sequences that are exactly complementary to the miRNA induce the RNA-mediated interference (RNAi) pathway. Messenger RNA targets are cleaved by ribonucleases in the ribonucleoprotein complex known as the RISC complex. This mechanism of miRNA-mediated gene silencing has been observed in plants (Hamilton and Baulcombe, Science, 286(5441):950-2 (1999) and Reinhart, et al., Genes and Dev., 16:1616-1626 (2002)), and in animals (Yekta, et al., Science, 304(5670):594-6 (2004)). In the second mechanism, miRNAs that bind to imperfect complementary sites on messenger RNA transcripts direct gene regulation at the posttranscriptional level but do not cleave their mRNA targets. MiRNAs identified in both plants and animals use this mechanism to exert translational control of their gene targets (Bartel, Cell, 116(2):281-97 (2004)).

Preferred miRNAs have at least 80%, typically at least 90%, even more typically at least 95% sequence identity with the target mRNA. Naturally occurring microRNAs that regulate target RNAs, pri-miRNA, pre-miRNA, mature miRNA or fragments of variants thereof that retain the biological activity of the mature miRNA and DNA encoding a pri-miRNA, pre-miRNA, mature miRNA, fragments or variants thereof, or regulatory elements of the miRNA, have been identified. The size of the miRNA is typically from 21 nucleotides to 170 nucleotides, although nucleotides of up to 2000 nucleotides can be utilized. In a preferred embodiment the size range of the pre-miRNA is between 70 to 170 nucleotides in length and the mature miRNA is between 21 and 25 nucleotides in length.

iii. piRNA

Studies have revealed a class of 24- to 30-nt RNAs that are generated by a Dicer-independent mechanism and that interact with a subset of Argonaute proteins related to Piwi. Studies in Drosophila have identified five Argonaute proteins: Ago1, Ago2, Ago3, Piwi, and Aubergine (Aub). Ago1 and Ago2 are ubiquitously expressed, whereas the expression of Piwi, Aub, and Ago3 are germ line-specific. Ago1 associates with miRNAs to regulate endogenous gene expression, and Ago2 serves as the slicer for siRNA-mediated gene silencing. Piwi, Aub, and Ago3 have been reported to interact with 24- to 30-nt small RNAs known as rasiRNAs. Murine Ago1, Ago2, Ago3, and Ago4 are associated with miRNAs, while the Piwi orthologs, MIWI, MILL and MIWI2, are found in germ line cells.

Like other members of the Ago family, Piwi proteins associate with small RNAs that act as guides in silencing target mRNA. These Piwi-interacting RNAs are called piRNAs. These small RNAs associated with Piwi RNPs have been cloned and sequence analysis of piRNAs shows a high percentage of uridine residues at the 5' termini (Gunawardane, et al., Science, 315(5818):1587-90 (2007), and genomic mapping shows that piRNAs are concentrated at a few loci (Brennecke et al., Cell, 128(6):1089-103 (2007)).

Primary transcripts for piRNAs are generated from the transposon regulatory regions of heterochromatin. These piRNAs are anti-sense, or complementary to transposon transcripts, and associated with both Piwi and Aub to trigger the amplification loop. Piwi/Aub cleaves target transposon transcripts between 10 and 11 nt from the 5' end of anti-sense piRNA and subsequently generates Ago3-associated sense piRNA. Ago3 functions as another slicer, which recognizes the complementary sequence of piRNA cluster transcripts, and generates more Piwi/Aub-associated anti-sense strand piRNA. piRNAs are thought to function with Piwis endogenously to maintain transposon silencing.

iv. External Guide Sequences (EGSs)

Ribonuclease P (RNase P) is a ribonucleoprotein complex found in all organisms. It is highly active in cells and is responsible for the maturation of 5' termini of all tRNAs, which account for approximately 2% of total cellular RNA. Human RNase P has at least nine polypeptides and a RNA subunit (H1 RNA). One of the unique features of RNase P is its ability to recognize structures, rather than the sequences, of substrates. This allows RNase P to hydrolyze different natural substrates in vivo or in vitro. Accordingly, any complex of two RNA molecules that resembles a tRNA molecule can be recognized and cleaved by RNase P. One of the RNA molecules is called the external guide sequence (EGS). An mRNA sequence can be targeted for RNase P cleavage by using EGSs to hybridize with the target RNA and direct RNase P to the site of cleavage. The EGSs used to direct human RNase P for targeted cleavage resemble three-quarters of a tRNA molecule and consist of two sequence elements: a targeting sequence complementary to the mRNA sequence and a guide sequence, which is a portion of the natural tRNA sequence and is required for RNase P recognition.

An EGS is designed to base pair through hydrogen bonding mechanism with a target mRNA to form a molecular structure similar to that of a transfer RNA (tRNA). The EGS/mRNA target is then cleaved and inactivated by RNAse P. EGS are not consumed in this reaction, but instead can recycle as a catalyst through multiple cycles of target mRNA cleavage leading to target inactivation more effectively than conventional anti-sense DNA oligonucleotides. EGS combine the specificity of conventional antisense DNA for gene targeting with the catalytic potency of RNAse P. RNAse P is present in abundant quantities in all viable eukaryotic cells where it serves to process transfer RNA (tRNA) by cleavage of a precursor transcript.

Small RNA sequences have been described that target eukaryotic mRNA for degradation by endogenous RNAse P, a ubiquitous cellular enzyme that generates mature transfer RNA (tRNA) from precursor transcripts (Gopalan, et al., *J. Biol. Chem.*, 277:6759-6762 (2002); Guerrier-Takada and Altman, *Methods Enzymol.*, 313:442-456 (2000); and Plehn-Dujowich and Altman, *PNAS USA*, 95:7327-7332 (1998)). A small RNA termed an External Guide Sequence (EGS) can be designed that mimics certain structural features of a tRNA molecule when it forms a bimolecular complex with another RNA sequence contained within a cellular messenger RNA (mRNA). Thus, any mRNA can in principle be recognized as a substrate for RNAse P with both the EGS and RNAse P participating as cocatalysts although due to the complexity of the binding and cleavage steps the kinetics of the reaction are difficult to predict in vitro or in vivo (Gopalan, et al., *J. Biol. Chem.*, 277:6759-6762 (2002) and Guerrier-Takada and Altman, *Methods Enzymol.*, 313:442-456 (2000)).

Design of an EGS requires both knowledge of the mRNA primary sequence to be cleaved by RNAse P as well as the secondary structure of the mRNA sequences in the mRNA. EGS sequences must be complementary to the primary sequence of the targeted mRNA and the sequences in the mRNA must be exposed in a single-stranded conformation within the mRNA secondary structure in order to bind to the EGS. Secondary structure of target mRNA can be approximated by computer modeling or determined empirically using nucleases or other RNA cleaving reagents well known to one of ordinary skill in the art. This analysis may be useful in locating regions of mRNA for targeting with complementary oligonucleotides including conventional DNA antisense oligonucleotides and catalytic RNA.

RNAase P is a ribonucleoprotein having two components, an RNA component and a protein component. The RNA component of RNAase P is responsible for the catalytic cleavage which forms the mature 5' ends of all transfer RNAs. RNAase P is endogenous to all living cells that have been examined. During the studies on recognition of substrate by RNAase P, it was found that *E. coli* RNAase P can cleave synthetic tRNA-related substrates that lack certain domains, specifically, the D, TψC and anticodon stems and loops, of the normal tRNA structure. For bacterial RNAse P a half-turn of an RNA helix and a 3' proximal CCA sequence contain sufficient recognition elements to allow the reaction to proceed. Using these principles, any RNA sequence can be converted into a substrate for bacterial RNAase P by using an external guide sequence, having at its 5' terminus nucleotides complementary to the nucleotides 3' to the cleavage site in the RNA to be cleaved and at its 5' terminus the nucleotides NCCA (N is any nucleotide).

EGS for promoting RNAase P-mediated cleavage of RNA has also been developed for use in eukaryotic systems as described by U.S. Pat. No. 5,624,824 to Yuan, et al., U.S. Pat. No. 6,610,478 to Takle, et al., WO 93/22434 to Yale University, WO 95/24489 to Yale University, and WO 96/21731 to Innovir Laboratories, Inc. As used herein, "external guide sequence" and "EGS" refer to any oligonucleotide or oligonucleotide analog that forms, in combination with a target RNA, a substrate for RNAase P.

An external guide sequence for promoting cleavage by RNAase P contains sequences which are complementary to the target RNA and which forms secondary and tertiary structures similar to portions of a tRNA molecule. In eukaryotes, including mammals, tRNAs are encoded by families of genes that are 73 to 150 base pairs long. tRNAs assume a secondary structure with four base paired stems known as the cloverleaf structure. The tRNA contains a stem, a D loop, a Variable loop, a TψC loop, and an anticodon loop. In one form, the EGS contains at least seven nucleotides which base pair with the target sequence 3' to the intended cleavage site to form a structure like the stem, nucleotides which base pair to form stem and loop structures similar to the TψC loop, the Variable loop and the anticodon loop, followed by at least three nucleotides that base pair with the target sequence to form a structure like the D loop.

Preferred guide sequences for eukaryotic RNAase P consist of a sequence which, when in a complex with the target RNA molecule, forms a secondary structure resembling that of a tRNA cloverleaf or parts thereof. The desired secondary structure is determined using conventional Watson-Crick base pairing schemes to form a structure resembling a tRNA. Since RNAse P recognizes structures as opposed to sequences, the specific sequence of the hydrogen bonded regions is less critical than the desired structure to be formed. The EGS and the target RNA substrate should resemble a sufficient portion of the tRNA secondary and tertiary structure to result in cleavage of the target RNA by RNAase P. The sequence of the EGS can be derived from any tRNA. The sequences and structures of a large number of tRNAs are well known to one of ordinary skill in the art. The consensus sequence for RNAse P recognition of tRNA molecules is GNNNNNU. The sequence obtained from the stem of the tRNA is altered to be complementary to the identified target RNA sequence. Target RNA is mapped by techniques well known to one of ordinary skill in the art for the consensus sequence. Such techniques include digestion of the target mRNA with T1 nuclease. Digestion with T1 nuclease cleaves RNA after guanine (G) residues that are exposed in solution and single-stranded, but not after G residues that are buried in the RNA secondary structure or base paired into double-stranded regions. The reaction products form a ladder after size fractionantion by gel-electrophoresis. A T1 sensitive site is detected as a dark band is compared to the target mRNA sequence to identify RNAse P consensus sequences. The complimentary sequence from the target mRNA is used for the EGS. The complementary sequences may consist of as few as seven nucleotides, but preferably include eleven nucleotides, in two sections which base pair with the target sequence and which are preferably separated by two unpaired nucleotides in the target sequence, preferably UU, wherein the two sections are complementary to a sequence 3' to the site targeted for cleavage.

The remaining portion of the guide sequence, which is required to cause RNAase P catalytic RNA to interact with the EGS/target RNA complex, is herein referred to as an RNAase P binding sequence. The anticodon loop and the Variable loop can be deleted and the sequence of the TψC loop can be changed without decreasing the usefulness of the guide sequence. External guide sequences can also be derived using in vitro evolution techniques (see U.S. Pat. No. 5,624,824 to Yuan, et al. and WO 95/24489 to Yale University).

v. Ribozymes and Other Catalytic RNAs

In another embodiment, the inhibitory RNA is a catalytic RNA, or a ribozyme. Ribozymes are described, for example, in PCT International Publication WO 90/11364, and in Sarver et al, *Science*, 247:1222-1225 (1990). While ribozymes that cleave mRNA at site specific recognition sequences can be used to degrade target mRNAs the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature, 334:585-591 (1988). There are usually numerous potential hammerhead ribozyme cleavage sites within each nucleotide sequence of a target mRNA of known sequence. Preferably, the ribozyme is engineered so that the cleavage recognition site is located near the 5' end of the target mRNA. This functions to increase efficiency and minimize the intracellular accumulation of non-functional mRNA transcripts.

B. Polymeric Nanoparticles

Nanoparticles generally refers to particles in the range of between 500 nm to less than 0.5 nm, preferably having a diameter that is between 50 and 500 nm, more preferably having a diameter that is between 50 and 300 nm. Cellular internalization of polymeric particles is highly dependent upon their size, with nanoparticulate polymeric particles being internalized by cells with much higher efficiency than micoparticulate polymeric particles. For example, Desai, et al. have demonstrated that about 2.5 times more nanoparticles that are 100 nm in diameter are taken up by cultured Caco-2 cells as compared to microparticles having a diameter on 1 μM (Desai, et al., *Pharm. Res.*, 14:1568-73 (1997)). Nanoparticles also have a greater ability to diffuse deeper into tissues in vivo.

The polymer that forms the core of the nanoparticle may be any biodegradable or non-biodegradable synthetic or natural polymer. In a preferred embodiment, the polymer is a biodegradable polymer. Nanoparticles are ideal materials for the fabrication of inhibitory RNA delivery vehicles: 1) control over the size range of fabrication, down to 100 nm or less, an important feature for passing through biological barriers; 2) reproducible biodegradability without the addition of enzymes or cofactors; 3) capability for sustained release of encapsulated, protected inhibitory RNAs over a period in the range of days to months by varying factors such as the monomer ratios or polymer size, for example, poly(lactic acid) (PLA) to poly(glycolic acid) (PGA) copolymer ratios, potentially abrogating the booster requirement (Gupta, et al., *Adv. Drug Deliv. Rev.*, 32(3):225-246 (1998); Kohn, et al., *J. Immunol. Methods*, 95(1):31-8 (1986); Langer, et al., *Adv. Drug Deliv. Rev.*, 28(1):97-119 (1997); Jiang, et al., *Adv. Drug Deliv. Rev.*, 57(3):391-410 (2005)), well-understood fabrication methodologies that offer flexibility over the range of parameters that can be used for fabrication, including choices of the polymer material, solvent, stabilizer, and scale of production; and 5) control over surface properties facilitating the introduction of modular functionalities into the surface.

Examples of preferred biodegradable polymers include synthetic polymers that degrade by hydrolysis such as poly (hydroxy acids), such as polymers and copolymers of lactic acid and glycolic acid, polyanhydrides, poly(ortho)esters, polyesters, polyurethanes, poly(butic acid), poly(valeric acid), poly(caprolactone), poly(hydroxyalkanoates), and poly(lactide-co-caprolactone).

Preferred natural polymers include alginate and other polysaccharides, collagen, albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

In some embodiments, non-biodegradable polymers can be used, especially hydrophobic polymers. Examples of preferred non-biodegradable polymers include ethylene vinyl acetate, poly(meth) acrylic acid, copolymers of maleic anhydride with other unsaturated polymerizable monomers, poly (butadiene maleic anhydride), polyamides, copolymers and mixtures thereof, and dextran, cellulose and derivatives thereof.

Other suitable biodegradable and non-biodegradable polymers include, but are not limited to, polyanhydrides, polyamides, polycarbonates, polyalkylenes, polyalkylene oxides such as polyethylene glycol, polyalkylene terepthalates such as poly(ethylene terephthalate), polyvinyl alcohols, polyvinyl ethers, polyvinyl esters, polyethylene, polypropylene, polyvinyl acetate), poly vinyl chloride, polystyrene, polyvinyl halides, polyvinylpyrrolidone, polymers of acrylic and methacrylic esters, polysiloxanes, polyurethanes and copolymers thereof, modified celluloses, alkyl cellulose, hydroxyalkyl celluloses, cellulose ethers, cellulose esters, nitro celluloses, cellulose acetate, cellulose propionate, cellulose acetate butyrate, cellulose acetate phthalate, carboxyethyl cellulose, cellulose triacetate, cellulose sulfate sodium salt, and polyacrylates such as poly(methyl methacrylate), poly (ethylmethacrylate), poly(butylmethacrylate), poly(isobutylmethacrylate), poly(hexylmethacrylate), poly(isodecylmethacrylate), poly(lauryl methacrylate), poly(phenyl methacrylate), poly(methyl acrylate), poly(isopropyl acrylate), poly(isobutyl acrylate), poly(octadecyl acrylate). These materials may be used alone, as physical mixtures (blends), or as co-polymers.

The polymer may be a bioadhesive polymer that is hydrophilic or hydrophobic. Hydrophilic polymers include CARBOPOL™ (a high molecular weight, crosslinked, acrylic acid-based polymers manufactured by NOVEON™), polycarbophil, cellulose esters, and dextran.

Release rate controlling polymers may be included in the polymer matrix or in the coating on the formulation. Examples of rate controlling polymers that may be used are hydroxypropylmethylcellulose (HPMC) with viscosities of either 5, 50, 100 or 4000 cps or blends of the different viscosities, ethylcellulose, methylmethacrylates, such as EUDRAGIT® RS100, EUDRAGIT® RL100, EUDRAGIT® NE 30D (supplied by Rohm America). Gastrosoluble polymers, such as EUDRAGIT® E100 or enteric polymers such as EUDRAGIT® L100-55D, L100 and S100 may be blended with rate controlling polymers to achieve pH dependent release kinetics. Other hydrophilic polymers such as alginate, polyethylene oxide, carboxymethylcellulose, and hydroxyethylcellulose may be used as rate controlling polymers.

These polymers can be obtained from sources such as Sigma Chemical Co., St. Louis, Mo.; Polysciences, Warrenton, Pa.; Aldrich, Milwaukee, Wis.; Fluka, Ronkonkoma, N.Y.; and BioRad, Richmond, Calif., or can be synthesized from monomers obtained from these or other suppliers using standard techniques.

In a preferred embodiment, the nanoparticles are formed of polymers fabricated from polylactides (PLA) and copolymers of lactide and glycolide (PLGA). These have established commercial use in humans and have a long safety record (Jiang, et al., *Adv. Drug Deliv. Rev.*, 57(3):391-410); Aguado and Lambert, *Immunobiology*, 184(2-3):113-25 (1992); Bramwell, et al., *Adv. Drug Deliv. Rev.*, 57(9):1247-65 (2005)). These polymers have been used to encapsulate siRNA (Yuan, et al., *Jour. Nanosocience and Nanotechnology*, 6:2821-8 (2006); Braden, et al., *Jour. Biomed. Nanotechnology*, 3:148-59 (2007); Khan, et al., *Jour. Drug Target*, 12:393-404 (2004)). Murata, et al., *J. Control. Release*, 126(3):246-54 (2008) showed inhibition of tumor growth after intratumoral injection of PLGA microspheres encapsulating siRNA targeted against vascular endothelial growth factor (VEGF). However, these microspheres were too large to be endocytosed (35-45 µm) (Conner and Schmid, *Nature*, 422 (6927):37-44 (2003)) and required release of the anti-VEGF siRNA extracellularly as a polyplex with either polyarginine or PEI before they could be internalized by the cell. These microparticles may have limited applications because of the toxicity of the polycations and the size of the particles. Nanoparticles (100-300 nm) of PLGA can penetrate deep into tissue and are easily internalized by many cells (Conner and Schmid, *Nature*, 422(6927):37-44 (2003)).

The nanoparticles are designed to release encapsulated inhibitory RNAs over a period of days to weeks. Factors that affect the duration of release include pH of the surrounding medium (higher rate of release at pH 5 and below due to acid catalyzed hydrolysis of PLGA) and polymer composition. Aliphatic polyesters differ in hydrophobicity, affecting degradation rate. Specifically, the hydrophobic poly(lactic acid) (PLA), more hydrophilic poly(glycolic acid) PGA and their copolymers, poly (lactide-co-glycolide) (PLGA) have various release rates. The degradation rate of these polymers, and often the corresponding drug release rate, can vary from days (PGA) to months (PLA) and is easily manipulated by varying the ratio of PLA to PGA.

Preferred nanoparticles are described in U.S. Publication No. 200610002852 and U.S. Publication No. 2006/0002971.

C. Polycations

In a preferred embodiment, the inhibitory RNAs are complexed to polycations to increase the encapsulation efficiency of the inhibitory RNAs into the nanoparticles. The term "polycation" refers to a compound having a positive charge, preferably at least 2 positive charges, at a selected pH, preferably physiological pH. Polycationic moieties have between about 2 to about 15 positive charges, preferably between about 2 to about 12 positive charges, and more preferably between about 2 to about 8 positive charges at selected pH values.

Many polycations are known in the art. Suitable constituents of polycations include basic amino acids and their derivatives such as arginine, asparagine, glutamine, lysine and histidine; cationic dendrimers; and amino polysaccharides. Suitable polycations can be linear, such as linear tetralysine, branched or dendrimeric in structure.

Exemplary polycations include, but are not limited to, synthetic polycations based on acrylamide and 2-acrylamido-2-methylpropanetrimethylamine, poly(N-ethyl-4-vinylpyridine) or similar quaternized polypyridine, diethylaminoethyl polymers and dextran conjugates, polymyxin B sulfate, lipopolyamines, poly(allylamines) such as the strong polycation poly(dimethyldiallylammonium chloride), polyethyleneimine, polybrene, and polypeptides such as protamine, the histone polypeptides, polylysine, polyarginine and polyornithine.

In one embodiment, the polycation is a polyamine. Polyamines are compounds having two or more primary amine groups. In a preferred embodiment, the polyamine is a naturally occurring polyamine that is produced in prokaryotic or eukaryotic cells. Naturally occurring polyamines represent compounds with cations that are found at regularly-spaced intervals and are therefore particularly suitable for complexing with nucleic acids. Polyamines play a major role in very basic genetic processes such as DNA synthesis and gene expression. Polyamines are integral to cell migration, proliferation and differentiation in plants and animals. The metabolic levels of polyamines and amino acid precursors are critical and hence biosynthesis and degradation are tightly regulated. Suitable naturally occurring polyamines include, but are not limited to, spermine, spermidine, cadaverine and putrescine. In a preferred embodiment, the polyamine is spermidine.

In another embodiment, the polycation is a cyclic polyamine. Cyclic polyamines are known in the art and are described, for example, in U.S. Pat. No. 5,698,546, WO 1993/012096 and WO 2002/010142. Exemplary cyclic polyamines include, but are not limited to, cyclen.

Spermine and spermidine are derivatives of putrescine (1,4-diaminobutane) which is produced from L-ornithine by action of ODC (ornithine decarboxylase). L-ornithine is the product of L-arginine degradation by arginase. Spermidine is a triamine structure that is produced by spermidine synthase (SpdS) which catalyzes monoalkylation of putrescine (1,4-diaminobutane) with decarboxylated S-adenosylmethionine (dcAdoMet) 3-aminopropyl donor. The formal alkylation of both amino groups of putrescine with the 3-aminopropyl donor yields the symmetrical tetraamine spermine. The biosynthesis of spermine proceeds to spermidine by the effect of spermine synthase (SpmS) in the presence of dcAdoMet. The 3-aminopropyl donor (dcAdoMet) is derived from S-adenosylmethionine by sequential transformation of L-methionine by methionine adenosyltransferase followed by decarboxylation by AdoMetDC (S-adenosylmethionine decarboxylase). Hence, putrescine, spermidine and spermine are metabolites derived from the amino acids L-arginine (L-ornithine, putrescine) and L-methionine (dcAdoMet, aminopropyl donor).

D. Coupling Agents or Ligands

The external surface of the polymeric nanoparticles may be modified by conjugating to, or incorporating into, the surface of the nanoparticle a coupling agent or ligand.

In a preferred embodiment, the coupling agent is present in high density on the surface of the nanoparticle. As used herein, "high density" refers to polymeric nanoparticles having a high density of ligands or coupling agents, which is preferably in the range of 1,000 to 10,000,000, more preferably 10,000-1,000,000 ligands per square micron of nanoparticle surface area. This can be measured by fluorescence staining of dissolved particles and calibrating this fluorescence to a known amount of free fluorescent molecules in solution.

Coupling agents associate with the polymeric nanoparticles and provide substrates that facilitate the modular assembly and disassembly of functional elements to the nanoparticles. Coupling agents or ligands may associate with nanoparticles through a variety of interactions including, but not limited to, hydrophobic interactions, electrostatic interactions and covalent coupling.

In a preferred embodiment, the coupling agents are molecules that match the polymer phase hydrophile-lipophile balance. Hydrophile-lipophile balances range from 1 to 15. Molecules with a low hydrophile-lipophile balance are more lipid loving and thus tend to make a water in oil emulsion while those with a high hydrophile-lipophile balance are more hydrophilic and tend to make an oil in water emulsion. Fatty acids and lipids have a low hydrophile-lipophile balance below 10.

Any amphiphilic polymer with a hydrophile-lipophile balance in the range 1-10, more preferably between 1 and 6, most preferably between 1 and up to 5, can be used as a coupling agent. Examples of coupling agents which may associate with polymeric nanoparticles via hydrophobic interactions include, but are not limited to, fatty acids, hydrophobic or amphipathic peptides or proteins, and polymers. These classes of coupling agents may also be used in any combination or ratio. In a preferred embodiment, the association of adaptor elements with nanoparticles facilitates a prolonged presentation of functional elements which can last for several weeks.

Coupling agents can also be attached to polymeric nanoparticles through covalent interactions through various functional groups. Functionality refers to conjugation of a molecule to the surface of the particle via a functional chemical group (carboxylic acids, aldehydes, amines, sulfhydryls and hydroxyls) present on the surface of the particle and present on the molecule to be attached.

Functionality may be introduced into the particles in two ways. The first is during the preparation of the nanoparticles, for example during the emulsion preparation of nanoparticles by incorporation of stabilizers with functional chemical groups. Suitable stabilizers include hydrophobic or amphipathic molecules that associate with the outer surface of the nanoparticles.

A second is post-particle preparation, by direct crosslinking particles and ligands with home- or heterobifunctional crosslinkers. This second procedure may use a suitable chemistry and a class of crosslinkers (CDI, EDAC, glutaraldehydes, etc. as discussed in more detail below) or any other crosslinker that couples ligands to the particle surface via chemical modification of the particle surface after preparation. This second class also includes a process whereby amphiphilic molecules such as fatty acids, lipids or functional stabilizers may be passively adsorbed and adhered to the particle surface, thereby introducing functional end groups for tethering to ligands.

One useful protocol involves the "activation" of hydroxyl groups on polymer chains with the agent, carbonyldiimidazole (CDI) in aprotic solvents such as DMSO, acetone, or THF. CDI forms an imidazolyl carbamate complex with the hydroxyl group which may be displaced by binding the free amino group of a molecule such as a protein. The reaction is an N-nucleophilic substitution and results in a stable N-alkylcarbamate linkage of the molecule to the polymer. The "coupling" of the molecule to the "activated" polymer matrix is maximal in the pH range of 9-10 and normally requires at least 24 hrs. The resulting molecule-polymer complex is stable and resists hydrolysis for extended periods of time.

Another coupling method involves the use of 1-ethyl-3-(3-dimethylaminopropyl) carbodiimide (EDAC) or "water-soluble CDI" in conjunction with N-hydroxylsulfosuccinimide (sulfa NHS) to couple the exposed carboxylic groups of polymers to the free amino groups of molecules in a totally aqueous environment at the physiological pH of 7.0. Briefly, EDAC and sulfo-NHS form an activated ester with the carboxylic acid groups of the polymer which react with the amine end of a molecule to form a peptide bond. The resulting peptide bond is resistant to hydrolysis. The use of sulfo-NHS in the reaction increases the efficiency of the EDAC coupling by a factor of ten-fold and provides for exceptionally gentle conditions that ensure the viability of the molecule-polymer complex.

By using either of these protocols it is possible to "activate" almost all polymers containing either hydroxyl or carboxyl groups in a suitable solvent system that will not dissolve the polymer matrix.

A useful coupling procedure for attaching molecules with free hydroxyl and carboxyl groups to polymers involves the use of the cross-linking agent, divinylsulfone. This method would be useful for attaching sugars or other hydroxylic compounds with bioadhesive properties to hydroxylic matrices. Briefly, the activation involves the reaction of divinylsulfone to the hydroxyl groups of the polymer, forming the vinylsulfonyl ethyl ether of the polymer. The vinyl groups will couple to alcohols, phenols and even amines. Activation and coupling take place at pH 11. The linkage is stable in the pH range from 1-8 and is suitable for transit through the intestine.

Any suitable coupling method known to those skilled in the art for the coupling of molecules and polymers with double bonds, including the use of UV crosslinking, may be used for attachment of molecules to the polymer.

In one embodiment, coupling agents can be conjugated to affinity tags. Affinity tags are any molecular species which form highly specific, noncovalent, physiochemical interactions with defined binding partners. Affinity tags which form highly specific, noncovalent, physiochemical interactions with one another are defined herein as "complementary". Suitable affinity tag pairs are well known in the art and include epitope/antibody, biotin/avidin, biotin/streptavidin, biotin/neutravidin, glutathione-S-transferase/glutathione, maltose binding protein/amylase and maltose binding protein/maltose. Examples of suitable epitopes which may be used for epitope/antibody binding pairs include, but are not limited to, HA, FLAG, c-Myc, glutathione-S-transferase, $His_6$, GFP, DIG, biotin and avidin. Antibodies (both monoclonal and polyclonal and antigen-binding fragments thereof) which bind to these epitopes are well known in the art.

Affinity tags that are conjugated to coupling agents allow for highly flexible, modular assembly and disassembly of functional elements which are conjugated to affinity tags which form highly specific, noncovalent, physiochemical interactions with complementary affinity tags which are conjugated to coupling agents. Adaptor elements may be conjugated with a single species of affinity tag or with any combination of affinity tag species in any ratio. The ability to vary the number of species of affinity tags and their ratios conjugated to adaptor elements allows for exquisite control over the number of functional elements which may be attached to the nanoparticles and their ratios.

In another embodiment, coupling agents are coupled directly to functional elements in the absence of affinity tags, such as through direct covalent interactions. Coupling agents can be covalently coupled to at least one species of functional element. Coupling agents can be covalently coupled to a single species of functional element or with any combination of species of functional elements in any ratio.

In a preferred embodiment, coupling agents are conjugated to at least one affinity tag that provides for assembly and disassembly of modular functional elements which are conjugated to complementary affinity tags. In a more preferred embodiment, coupling agents are fatty acids that are conjugated with at least one affinity tag. In a particularly preferred embodiment, the coupling agents are fatty acids conjugated with avidin or streptavidin. Avidin/streptavidin-conjugated fatty acids allow for the attachment of a wide variety of biotin-conjugated functional elements.

The coupling agents are preferably provided on, or in the surface of, nanoparticles at a high density. This high density of coupling agents allows for coupling of the polymeric nanoparticles to a variety of species of functional elements while still allowing for the functional elements to be present in high enough numbers to be efficacious.

1. Fatty Acids

The coupling agents may include fatty acids. Fatty acids may be of any acyl chain length and may be saturated or unsaturated. In a particularly preferred embodiment, the fatty acid is palmitic acid. Other suitable fatty acids include, but are not limited to, saturated fatty acids such as butyric, caproic, caprylic, capric, lauric, myristic, stearic, arachidic and behenic acid. Still other suitable fatty acids include, but are not limited to, unsaturated fatty acids such as oleic, linoleic, alpha-linolenic, arachidonic, eicosapentaenoic, docosahexaenoic and erucic acid.

ii. Hydrophobic or Amphipathic Peptides

The coupling agents may include hydrophobic or amphipathic peptides. Preferred peptides should be sufficiently hydrophobic to preferentially associate with the polymeric nanoparticle over the aqueous environment. Amphipathic polypeptides useful as adaptor elements may be mostly hydrophobic on one end and mostly hydrophilic on the other end. Such amphipathic peptides may associate with polymeric nanoparticles through the hydrophobic end of the peptide and be conjugated on the hydrophilic end to a functional group.

iii. Hydrophobic Polymers

Coupling agents may include hydrophobic polymers. Examples of hydrophobic polymers include, but are not limited to, polyanhydrides, poly(ortho)esters, and polyesters such as polycaprolactone.

E. Targeting Molecules

One class of functional elements that can be attached to the nanoparticles is targeting molecules. Targeting molecules can be proteins, peptides, nucleic acid molecules, saccharides or polysaccharides that bind to a receptor or other molecule on the surface of a targeted cell. The degree of specificity and the avidity of binding to the graft can be modulated through the selection of the targeting molecule. For example, antibodies are very specific. These can be polyclonal, monoclonal, fragments, recombinant, or single chain, many of which are commercially available or readily obtained using standard techniques. Table 1 is a list of ligand-targeted nanoparticulate systems providing examples of useful ligands and their targets.

TABLE 1

Selected list of ligand-targeted nanoparticulate systems evaluated for in vitro or in vivo therapeutics delivery

| Ligand | Drug | System | Target Cells | Evaluation |
|---|---|---|---|---|
| Nucleic acids | | | | |
| Aptamers[a] | | PLA | Prostate Epithelial cells | In vitro |
| ECM Proteins | | | | |
| Integrin[b] | Raf genes | Liposomes | Melanoma cells | In vivo |
| RGD peptides[c] | siRNA | poly(ethylene Imine) | tumor vasculature | In vivo |
| Fibrinogen[d] | radioisotopes | Albumin | tumor vasculature | In vivo |
| Lipids | | | | |
| MP Lipid A[e] | | PLGA | Dendritic cells | In vitro |
| Carbohydrates | | | | |
| Galactose[f] | retinoic acid | PLA | Hepatocytes | In vitro |
| Hyaluronic acid[g] | Doxorubicin | Liposomes | CD44+ melanoma cells | In vitro |
| Peptidomimetics[h] | Various | mPEG/PLGA | Brain cells | Various |
| Antibodies to: | | | | |
| HER2 receptor[i] | | gelatin/HAS | HER2 cells | In vitro |
| HER2 receptor[j] | Doxorubicin | Liposomes | HER2 cells | In vivo |
| CD19[k] | Doxorubicin | Liposomes | B cell lymphoma | In vivo |

TABLE 1-continued

Selected list of ligand-targeted nanoparticulate systems evaluated
for in vitro or in vivo therapeutics delivery

| Ligand | Drug | System | Target Cells | Evaluation |
|---|---|---|---|---|
| Vitamins | | | | |
| Folate[j] | Doxorubicin | Liposomes | Leukemia cells | In vivo |

[a]Park, J. W. et al. Clin Cancer Res 8, 1172-1181 (2002).
[b]Hood, J. D. et al. Science 296, 2404-2407 (2002).
[c]Schiffelers, R. M. et al. Nucleic Acids Res 32, e149 (2004).
[d]Hallahan, D. et al. Cancer Cell 3, 63-74 (2003).
[e]Elamanchili, et al. Vaccine 22, 2406-2412 (2004).
[f]Cho, C. S. et al. J Control Release 77, 7-15 (2001).
[g]Eliaz, R. E. & Szoka, F. C., Jr. Cancer Res 61, 2592-2601 (2001).
[h]Olivier, J. C. Neurorx 2, 108-119 (2005).
[i]Wartlick, H. et al. J Drug Target 12, 461-471 (2004).
[j]Park, J. W. et al. Clin Cancer Res 8, 1172-1181 (2002)
[k]Lopes de Menezes, et al. Cancer Res 58, 3320-3330 (1998).
[l]Pan, X. Q. et al. Blood 100, 594-602 (2002).

Examples of molecules targeting extracellular matrix ("ECM") include glycosaminoglycan ("GAG") and collagen. In one embodiment, the external surface of polymer microparticles may be modified to enhance the ability of the microparticles to interact with selected cells or tissue. The method described above wherein an adaptor element conjugated to a targeting molecule is inserted into the particle is preferred. However, in another embodiment, the outer surface of a polymer micro- or nanoparticle having a carboxy terminus may be linked to targeting molecules that have a free amine terminus.

Other useful ligands attached to polymeric micro- and nanoparticles include pathogen-associated molecular patterns (PAMPs). PAMPs target Toll-like Receptors (TLRs) on the surface of the cells or tissue, or signal the cells or tissue internally, thereby potentially increasing uptake. PAMPs conjugated to the particle surface or co-encapsulated may include: unmethylated CpG DNA (bacterial), double-stranded RNA (viral), lipopolysacharride (bacterial), peptidoglycan (bacterial), lipoarabinomannin (bacterial), zymosan (yeast), mycoplasmal lipoproteins such as MALP-2 (bacterial), flagellin (bacterial) poly(inosinic-cytidylic) acid (bacterial), lipoteichoic acid (bacterial) or imidazoquinolines (synthetic).

In another embodiment, the outer surface of the microparticle may be treated using a mannose amine, thereby mannosylating the outer surface of the microparticle. This treatment may cause the microparticle to bind to the target cell or tissue at a mannose receptor on the antigen presenting cell surface. Alternatively, surface conjugation with an immunoglobulin molecule containing an Fc portion (targeting Fc receptor), heat shock protein moiety (HSP receptor), phosphatidylserine (scavenger receptors), and lipopolysaccharide (LPS) are additional receptor targets on cells or tissue.

Lectins that can be covalently attached to micro- and nanoparticles to render them target specific to the mucin and mucosal cell layer include lectins isolated from *Abrus precatroius, Agaricus bisporus, Anguilla anguilla, Arachis hypogaea, Pandeiraea simplicifolia, Bauhinia purpurea, Caragan arobrescens, Cicer arietinum, Codium fragile, Datura stramonium, Dolichos biflorus, Erythrina corallodendron, Erythrina cristagalli, Euonymus europaeus, Glycine max, Helix aspersa, Helix pomatia, Lathyrus odoratus, Lens culinaris, Limulus polyphemus, Lysopersicon esculentum, Madura ponOra, Momordica charantia, Mycoplasma gallisepticum, Naja mocambique*, as well as the lectins Concanavalin A, Succinyl-Concanavalin A, *Triticum vulgaris, Ulex europaeus* I, II and III, *Sambucus nigra, Maackia amurensis, Limax fluvus, Homarus americanus, Cancer antennarius*, and *Lotus tetragonolobus*.

The choice of targeting molecule will depend on the method of administration of the nanoparticle composition and the cells or tissues to be targeted. The targeting molecule may generally increase the binding affinity of the particles for cell or tissues or may target the nanoparticle to a particular tissue in an organ or a particular cell type in a tissue. Avidin increases the ability of polymeric nanoparticles to bind to tissues. While the exact mechanism of the enhanced binding of avidin-coated particles to tissues has not been elucidated, it is hypothesized it is caused by electrostatic attraction of positively charged avidin to the negatively charged extracellular matrix of tissue. Non-specific binding of avidin, due to electrostatic interactions, has been previously documented and zeta potential measurements of avidin-coated PLGA particles revealed a positively charged surface as compared to uncoated PLGA particles.

The attachment of any positively charged ligand, such as polyethyleneimine or polylysine, to any polymeric particle may improve bioadhesion due to the electrostatic attraction of the cationic groups coating the beads to the net negative charge of the mucus. The mucopolysaccharides and mucoproteins of the mucin layer, especially the sialic acid residues, are responsible for the negative charge coating. Any ligand with a high binding affinity for mucin could also be covalently linked to most microparticles with the appropriate chemistry and be expected to influence the binding of microparticles to the gut. For example, polyclonal antibodies raised against components of mucin or else intact mucin, when covalently coupled to microparticles, would provide for increased bioadhesion. Similarly, antibodies directed against specific cell surface receptors exposed on the lumenal surface of the intestinal tract would increase the residence time of beads, when coupled to microparticles using the appropriate chemistry. The ligand affinity need not be based only on electrostatic charge, but other useful physical parameters such as solubility in mucin or else specific affinity to carbohydrate groups.

The covalent attachment of any of the natural components of mucin in either pure or partially purified form to the microparticles would decrease the surface tension of the bead-gut interface and increase the solubility of the bead in the mucin layer. The list of useful ligands includes, but is not limited to the following: sialic acid, neuraminic acid, n-acetyl-neuraminic acid, n-glycolylneuraminic acid, 4-acetyl-n- acetylneuraminic acid, diacetyl-n-acetylneuraminic acid, glucuronic acid, iduronic acid, galactose, glucose, mannose, fucose, any of the partially purified fractions prepared by chemical treatment of naturally occurring mucin, e.g., mucoproteins, mucopolysaccharides and mucopolysaccharide-protein complexes, and antibodies immunoreactive against proteins or sugar structure on the mucosal surface.

The attachment of polyamino acids containing extra pendant carboxylic acid side groups, e.g., polyaspartic acid and polyglutamic acid, should also provide a useful means of increasing bioadhesiveness. Using polyamino acids in the 15,000 to 50,000 kDa molecular weight range yields chains of 120 to 425 amino acid residues attached to the surface of the microparticles. The polyamino chains increase bioadhesion by means of chain entanglement in mucin strands as well as by increased carboxylic charge.

The efficacy of the nanoparticles is determined in part by their route of administration into the body. For orally and topically administered nanoparticles, epithelial cells constitute the principal barrier that separates an organism's interior from the outside world. Epithelial cells such as those that line the gastrointestinal tract form continuous monolayers that simultaneously confront the extracellular fluid compartment and the extracorporeal space.

Adherence to cells is an essential first step in crossing the epithelial barrier by any of these mechanisms. Therefore, in one embodiment, the nanoparticles disclosed herein further include epithelial cell targeting molecules. Epithelial cell targeting molecules include monoclonal or polyclonal antibodies or bioactive fragments thereof that recognize and bind to epitopes displayed on the surface of epithelial cells. Epithelial cell targeting molecules also include ligands which bind to a cell surface receptor on epithelial cells. Ligands include, but are not limited to, molecules such as polypeptides, nucleotides and polysaccharides.

A variety of receptors on epithelial cells may be targeted by epithelial cell targeting molecules. Examples of suitable receptors to be targeted include, but are not limited to, IgE Fc receptors, EpCAM, selected carbohydrate specificities, dipeptidyl peptidase, and E-cadherin.

F. Protein Transduction Domains and Fusogenic Peptides

Additional classes of functional elements that can be attached to the nanoparticles include protein transduction domains and fusogenic peptides.

"Protein Transduction Domain" or PTD refers to a polypeptide, polynucleotide, or organic or inorganic compounds that facilitates traversing a lipid bilayer, micelle, cell membrane, organelle membrane, or vesicle membrane. A PTD attached to another molecule facilitates the molecule traversing membranes, for example going from extracellular space to intracellular space, or cytosol to within an organelle. Exemplary PTDs include, but are not limited, to HIV TAT (YGRKKRRQRRR (SEQ ID NO:10) or RKKRRQRRR (SEQ ID NO:11), 11 arginine residues, VP22 peptide, and an ANTp peptide (RQIKIWFQNRRMKWKK) (SEQ ID NO:12) or positively charged polypeptides or polynucleotides having 8-15 residues, preferably 9-11 residues. Short, non-peptide polymers that are rich in amines or guanidinium groups are also capable of carrying molecules crossing biological membranes.

A "fusogenic peptide" is any peptide with membrane destabilizing abilities. In general, fusogenic peptides have the propensity to form an amphiphilic alpha-helical structure when in the presence of a hydrophobic surface such as a membrane. The presence of a fusogenic peptide induces formation of pores in the cell membrane by disruption of the ordered packing of the membrane phospholipids. Some fusogenic peptides act to promote lipid disorder and in this way enhance the chance of merging or fusing of proximally positioned membranes of two membrane enveloped particles of various nature (e.g. cells, enveloped viruses, liposomes). Other fusogenic peptides may simultaneously attach to two membranes, causing merging of the membranes and promoting their fusion into one. Examples of fusogenic peptides include a fusion peptide from a viral envelope protein ectodomain, a membrane-destabilizing peptide of a viral envelope protein membrane-proximal domain from the cytoplasmic tails.

Other fusogenic peptides often also contain an amphiphilic-region. Examples of amphiphilic-region containing peptides include: melittin, magainins, the cytoplasmic tail of HIV1 gp41, microbial and reptilian cytotoxic peptides such as bomolitin 1, pardaxin, mastoparan, crabrolin, cecropin, entamoeba, and staphylococcal .alpha.-toxin; viral fusion peptides from (1) regions at the N terminus of the transmembrane (TM) domains of viral envelope proteins, e.g. HIV-1, SW, influenza, polio, rhinovirus, and coxsackie virus; (2) regions internal to the TM ectodomain, e.g. semliki forest virus, sindbis virus, rota virus, rubella virus and the fusion peptide from sperm protein PH-30: (3) regions membrane-proximal to the cytoplasmic side of viral envelope proteins e.g. in viruses of avian leukosis (ALV), Feline immunodeficiency (FIV), Rous Sarcoma (RSV), Moloney murine leukemia virus (MoMuLV), and spleen necrosis (SNV).

G. Contrast Agents and Other Markers

Optionally, the nanoparticles disclosed herein may further include agents useful for determining the location of administered particles. Agents useful for this purpose include fluorescent tags, radionuclides and contrast agents.

Suitable imaging agents include, but are not limited to, fluorescent molecules such as those described by Molecular Probes (Handbook of fluorescent probes and research products), such as Rhodamine, fluorescein, Texas red, Acridine Orange, Alexa Fluor (various), Allophycocyanin, 7-aminoactinomycin D, BOBO-1, BODIPY (various), Calcien, Calcium Crimson, Calcium green, Calcium Orange, 6-carboxyrhodamine 6G, Cascade blue, Cascade yellow, DAPI, DiA, DiD, Dil, DiO, DiR, ELF 97, Eosin, ER Tracker Blue-White, EthD-1, Ethidium bromide, Fluo-3, Fluo4, FM1-43, FM4-64, Fura-2, Fura Red, Hoechst 33258, Hoechst 33342, 7-hydroxy-4-methylcoumarin, Indo-1, JC-1, JC-9, JOE dye, Lissamine rhodamine B, Lucifer Yellow CH, LysoSensor Blue DND-167, LysoSensor Green, LysoSensor Yellow/Blu, Lysotracker Green FM, Magnesium Green, Marina Blue, Mitotracker Green FM, Mitotracker Orange CMTMRos, MitoTracker Red CMXRos, Monobromobimane, NBD amines, NeruoTrace 500/525 green, Nile red, Oregon Green, Pacific Blue. POP-1, Propidium iodide, Rhodamine 110, Rhodamine Red, R-Phycoerythrin, Resorfin, RH414, Rhod-2, Rhodamine Green, Rhodamine 123, ROX dye, Sodium Green, SYTO blue (various), SYTO green (Various), SYTO orange (various), SYTOX blue, SYTOX green, SYTOX orange, Tetramethylrhodamine B, TOT-1, TOT-3, X-rhod-1, YOYO-1, YOYO-3.

Additionally radionuclides can be used as imaging agents. Suitable radionuclides include, but are not limited to radioactive species of Fe(III), Fe(II), Cu(II), Mg(II), Ca(II), and Zn(II) Indium, Gallium and Technetium. Other suitable contrast agents include metal ions generally used for chelation in paramagnetic T1-type MIR contrast agents, and include di- and tri-valent cations such as copper, chromium, iron, gadolinium, manganese, erbium, europium, dysprosium and holmium, Metal ions that can be chelated and used for radionuclide imaging, include, but are not limited to metals such as gallium, germanium, cobalt, calcium, indium, iridium, rubidium, yttrium, ruthenium, yttrium, technetium, rhenium, platinum, thallium and samarium. Additionally metal ions known to be useful in neutron-capture radiation therapy include boron and other metals with large nuclear cross-sections. Also suitable are metal ions useful in ultrasound contrast, and X-ray contrast compositions.

Examples of other suitable contrast agents include gases or gas emitting compounds, which are radioopaque.

H. Pharmaceutically Acceptable Excipients

The compositions may be administered in combination with a physiologically or pharmaceutically acceptable carrier, excipient, or stabilizer. The term "pharmaceutically acceptable" means a non-toxic material that does not interfere with the effectiveness of the biological activity of the active ingredients. The term "pharmaceutically-acceptable carrier" means one or more compatible solid or liquid fillers, dilutants or encapsulating substances which are suitable for administration to a human or other vertebrate animal. The term "carrier" refers to an organic or inorganic ingredient, natural or synthetic, with which the active ingredient is combined to facilitate the application.

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. In the preferred embodiment, administration is by injection. Typical formulations for injection include a carrier such as sterile saline or a phosphate buffered saline. Viscosity modifying agents and preservatives are also frequently added.

Optional pharmaceutically acceptable excipients especially for enteral, topical and mucosal administration, include, but are not limited to, diluents, binders, lubricants, disintegrants, colorants, stabilizers, and surfactants. Diluents, also referred to as "fillers", are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (POLYPLASDONE® XL from GAF Chemical Corp).

Stabilizers are used to inhibit or retard decomposition reactions which include, by way of example, oxidative reactions.

Surfactants may be anionic, cationic, amphoteric or non-ionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl mono isopropanolamide, and polyoxyethylene hydrogenated tallow amide. Examples of amphoteric surfactants include sodium N-dodecyl-b-alanine, sodium N-lauryl-b-iminodipropionate, myristoamphoacetate, lauryl betaine and lauryl sulfobetaine.

If desired, the particles may also contain minor amount of nontoxic auxiliary substances such as wetting or emulsifying agents, dyes, pH buffering agents, or preservatives.

The nanoparticles may be complexed with other agents. The pharmaceutical compositions may take the form of, for example, tablets or capsules prepared by conventional means with pharmaceutically acceptable excipients such as binding agents (e.g., acacia, methylcellulose, sodium carboxymethylcellulose, polyvinylpyrrolidone (Povidone), hydroxypropyl methylcellulose, sucrose, starch, and ethylcellulose); fillers (e.g., corn starch, gelatin, lactose, acacia, sucrose, microcrystalline cellulose, kaolin, mannitol, dicalcium phosphate, calcium carbonate, sodium chloride, or alginic acid); lubricants (e.g. magnesium stearates, stearic acid, silicone fluid, talc, waxes, oils, and colloidal silica); and disintegrators (e.g. micro-crystalline cellulose, corn starch, sodium starch glycolate and alginic acid. If water-soluble, such formulated complex then may be formulated in an appropriate buffer, for example, phosphate buffered saline or other physiologically compatible solutions. Alternatively, if the resulting complex has poor solubility in aqueous solvents, then it may be formulated with a non-ionic surfactant such as TWEEN™, or polyethylene glycol. Thus, the compounds and their physiologically acceptable solvates may be formulated for administration.

Liquid formulations for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the active compound(s), wetting agents, sweeteners, and coloring and flavoring agents. Various liquid and powder formulations can be prepared by conventional methods for inhalation by the patient.

The nanoparticles may be further coated. Suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Röhm Pharma, Darmstadt, Germany), zein, shellac, and polysaccharides. Additionally, the coating material may contain conventional carriers such as plasticizers, pigments, colorants, glidants, stabilization agents, pore formers and surfactants.

III. Methods of Manufacture

A. Methods of Making Microparticles

The nanoparticle compositions described herein can be prepared by a variety of methods. The inhibitory RNA is first complexed to a polycation. Complexation can be achieved by mixing the inhibitory RNAs and polycations at an appropriate molar ratio. When a polyamine is used as the polycation species, it is useful to determine the molar ratio of the polyamine nitrogen to the polynucleotide phosphate (N/P ratio). In a preferred embodiment, inhibitory RNAs and polyamines are mixed together to form a complex at an N/P ratio of between approximately 8:1 to 15:1. The volume of polyamine solution required to achieve particular molar ratios can be determined according to the following formula:

$$V_{NH2} = \frac{C_{inhRNA,final} \times M_{w,inhRNA} / C_{inhRNA,final} \times M_{w,P} \times \Phi_{N:P} \times \Phi V_{final}}{C_{NH2} / M_{w,NH2}}$$

where $M_{w,inhRNA}$=molecular weight of inhibitory RNA, $M_{w,P}$=molecular weight of phosphate groups of inhibitory RNA, $\Phi_{N:P}$=N:P ratio (molar ratio of nitrogens from polyamine to the ratio of phosphates from the inhibitory RNA), $C_{NH2}$, stock=concentration of polyamine stock solution, and $M_{w,NH2}$=molecular weight per nitrogen of polyamine.

Polycation complexation with inhibitory RNAs can be achieved by mixing solutions containing polycations with solutions containing inhibitory RNAs. The mixing can occur at any appropriate temperature. In one embodiment, the mixing occurs at room temperature. The mixing can occur with mild agitation, such as can be achieved through the use of a rotary shaker.

In a preferred embodiment, the nanoparticles are formed by a double-emulsion solvent evaporation technique, such as that described by Fahmy, et al. (Fahmy, et al., *Biomaterials*, 26:5727-36 (2005)). In this technique, the siRNA/polycation complexes are reconstituted in an aqueous solution. This aqueous solution is then added dropwise to a polymer solution of a desired polymer dissolved in an organic solvent to form the first emulsion. This mixture is then added dropwise to solution containing a surfactant, such as polyvinyl alcohol (PVA) and sonicated to form the double emulsion. The final emulsion is then poured into a solution containing the surfactant in an aqueous solution and stirred for a period of time to allow the dichloromethane to evaporate and the particles to harden. The concentration of the surfactant used to form the emulsion, and the sonication time and amplitude can be optimized according to principles known in the art for formulating particles with a desired diameter. The particles can be collected by centrifugation. If it is desirable to store the nanoparticles for later use, they can be rapidly frozen, and lyophilized.

Additional techniques for encapsulating the inhibitory RNA and polycation complex into polymeric nanoparticles are described below.

1. Solvent Evaporation

In this method the polymer is dissolved in a volatile organic solvent, such as methylene chloride. The drug (either soluble or dispersed as fine particles) is added to the solution, and the mixture is suspended in an aqueous solution that contains a surface active agent such as poly(vinyl alcohol). The resulting emulsion is stirred until most of the organic solvent evaporated, leaving solid microparticles. The resulting microparticles are washed with water and dried overnight in a lyophilizer. Microparticles with different sizes (0.5-1000 microns) and morphologies can be obtained by this method. This method is useful for relatively stable polymers like polyesters and polystyrene.

However, labile polymers, such as polyanhydrides, may degrade during the fabrication process due to the presence of water. For these polymers, the following two methods, which are performed in completely anhydrous organic solvents, are more useful.

2. Interfacial Polycondensation

Interfacial polycondensation is used to microencapsulate a core material in the following manner. One monomer and the core material are dissolved in a solvent. A second monomer is dissolved in a second solvent (typically aqueous) which is immiscible with the first. An emulsion is formed by suspending the first solution through stirring in the second solution. Once the emulsion is stabilized, an initiator is added to the aqueous phase causing interfacial polymerization at the interface of each droplet of emulsion.

3. Solvent Evaporation Microencapsulation

In solvent evaporation microencapsulation, the polymer is typically dissolved in a water immiscible organic solvent and the material to be encapsulated is added to the polymer solution as a suspension or solution in an organic solvent. An emulsion is formed by adding this suspension or solution to a beaker of vigorously stirring water (often containing a surface active agent, for example, polyethylene glycol or polyvinyl alcohol, to stabilize the emulsion). The organic solvent is evaporated while continuing to stir. Evaporation results in precipitation of the polymer, forming solid microcapsules containing core material.

The solvent evaporation process can be used to entrap a liquid core material in a polymer such as PLA, PLA/PGA copolymer, or PLA/PCL copolymer microcapsules. The polymer or copolymer is dissolved in a miscible mixture of solvent and nonsolvent, at a nonsolvent concentration which is immediately below the concentration which would produce phase separation (i.e., cloud point). The liquid core material is added to the solution while agitating to form an emulsion and disperse the material as droplets. Solvent and nonsolvent are vaporized, with the solvent being vaporized at a faster rate, causing the polymer or copolymer to phase separate and migrate towards the surface of the core material droplets. This phase-separated solution is then transferred into an agitated volume of nonsolvent, causing any remaining dissolved polymer or copolymer to precipitate and extracting any residual solvent from the formed membrane. The result is a microcapsule composed of polymer or copolymer shell with a core of liquid material.

Solvent evaporation microencapsulation can result in the stabilization of insoluble active agent particles in a polymeric solution for a period of time ranging from 0.5 hours to several months. Stabilizing an insoluble pigment and polymer within the dispersed phase (typically a volatile organic solvent) can be useful for most methods of microencapsulation that are dependent on a dispersed phase, including film casting, solvent evaporation, solvent removal, spray drying, phase inversion, and many others.

The stabilization of insoluble active agent particles within the polymeric solution could be critical during scale-up. By stabilizing suspended active agent particles within the dispersed phase, the particles can remain homogeneously dispersed throughout the polymeric solution as well as the resulting polymer matrix that forms during the process of microencapsulation.

Solvent evaporation microencapsulation (SEM) have several advantages. SEM allows for the determination of the best polymer-solvent-insoluble particle mixture that will aid. in the formation of a homogeneous suspension that can be used to encapsulate the particles. SEM stabilizes the insoluble particles or pigments within the polymeric solution, which will help during scale-up because one will be able to let suspensions of insoluble particles or pigments sit for long periods of time, making the process less time-dependent and less labor intensive. SEM allows for the creation of nanoparticles that have a more optimized release of the encapsulated material.

4. Hot Melt Microencapsulation

In this method, the polymer is first melted and then mixed with the solid particles. The mixture is suspended in a non-miscible solvent (like silicon oil), and, with continuous stirring, heated to 5° C. above the melting point of the polymer. Once the emulsion is stabilized, it is cooled until the polymer particles solidify. The resulting microparticles are washed by decantation with petroleum ether to give a free-flowing powder. Microparticles with sizes between 0.5 to 1000 microns are obtained with this method. The external surfaces of spheres prepared with this technique are usually smooth and dense. This procedure is used to prepare microparticles made of polyesters and polyanhydrides. However, this method is limited to polymers with molecular weights between 1,000-50,000.

5. Solvent Removal Microencapsulation

In solvent removal microencapsulation, the polymer is typically dissolved in an oil miscible organic solvent and the material to be encapsulated is added to the polymer solution as a suspension or solution in organic solvent. Surface active agents can be added to improve the dispersion of the material to be encapsulated. An emulsion is formed by adding this suspension or solution to vigorously stirring oil, in which the oil is a nonsolvent for the polymer and the polymer/solvent solution is immiscible in the oil. The organic solvent is removed by diffusion into the oil phase while continuing to stir. Solvent removal results in precipitation of the polymer, forming solid microcapsules containing core material.

6. Phase Separation Microencapsulation

In phase separation microencapsulation, the material to be encapsulated is dispersed in a polymer solution with stirring. While continually stirring to uniformly suspend the material, a nonsolvent for the polymer is slowly added to the solution to decrease the polymer's solubility. Depending on the solubility of the polymer in the solvent and nonsolvent, the polymer either precipitates or phase separates into a polymer rich and a polymer poor phase. Under proper conditions, the polymer in the polymer rich phase will migrate to the interface with the continuous phase, encapsulating the core material in a droplet with an outer polymer shell.

7. Spontaneous Emulsification

Spontaneous emulsification involves solidifying emulsified liquid polymer droplets by changing temperature, evaporating solvent, or adding chemical cross-linking agents. The physical and chemical properties of the encapsulant, and the material to be encapsulated, dictates the suitable methods of encapsulation. Factors such as hydrophobicity, molecular weight, chemical stability, and thermal stability affect encapsulation.

8. Coacervation

Encapsulation procedures for various substances using coacervation techniques have been described in the prior art, for example, in GB-B-929 406; GB-B-929 401; U.S. Pat. Nos. 3,266,987; 4,794,000 and 4,460,563. Coacervation is a process involving separation of colloidal solutions into two or more immiscible liquid layers (Ref. Dowben, R. General Physiology, Harper & Row, New York, 1969, pp. 142-143.). Through the process of coacervation compositions comprised of two or more phases and known as coacervates may be produced. The ingredients that comprise the two phase coacervate system are present in both phases; however, the colloid rich phase has a greater concentration of the components than the colloid poor phase.

9. Solvent Removal

This technique is primarily designed for polyanhydrides. In this method, the drug is dispersed or dissolved in a solution of the selected polymer in a volatile organic solvent like methylene chloride. This mixture is suspended by stirring in an organic oil (such as silicon oil) to form an emulsion. Unlike solvent evaporation, this method can be used to make microparticles from polymers with high melting points and different molecular weights. Microparticles that range between 1-300 microns can be obtained by this procedure. The external morphology of spheres produced with this technique is highly dependent on the type of polymer used.

10. Spray-Drying

In this method, the polymer is dissolved in organic solvent. A known amount of the active drug is suspended (insoluble drugs) or co-dissolved (soluble drugs) in the polymer solution. The solution or the dispersion is then spray-dried. Typical process parameters for a mini-spray drier (Buchi) are as follows: polymer concentration=0.04 g/mL, inlet temperature=−24° C., outlet temperature=13-15° C., aspirator setting=15, pump setting=10 mL/minute, spray flow=600 Nl/hr, and nozzle diameter=0.5 mm. Microparticles ranging between 1-10 microns are obtained with a morphology which depends on the type of polymer used.

B. Molecules to be Encapsulated or Attached to the Surface of the Particles

There are two principle groups of molecules to be encapsulated or attached to the polymer, either directly or via a coupling molecule: targeting molecules, attachment molecules and therapeutic, nutritional, diagnostic or prophylactic agents. These can be coupled using standard techniques. The targeting molecule or therapeutic molecule to be delivered can be coupled directly to the polymer or to a material such as a fatty acid which is incorporated into the polymer.

Functionality refers to conjugation of a ligand to the surface of the particle via a functional chemical group (carboxylic acids, aldehydes, amines, sulfhydryls and hydroxyls) present on the surface of the particle and present on the ligand to be attached. Functionality may be introduced into the particles in two ways. The first is during the preparation of the microparticles, for example during the emulsion preparation of microparticles by incorporation of stabilizers with functional chemical groups. Example 1 demonstrates this type of process whereby functional amphiphilic molecules are inserted into the particles during emulsion preparation.

A second is post-particle preparation, by direct crosslinking particles and ligands with homo- or heterobifunctional crosslinkers. This second procedure may use a suitable chemistry and a class of crosslinkers (CDI, EDAC, glutaraldehydes, etc. as discussed in more detail below) or any other crosslinker that couples ligands to the particle surface via chemical modification of the particle surface after preparation. This second class also includes a process whereby amphiphilic molecules such as fatty acids, lipids or functional stabilizers may be passively adsorbed and adhered to the particle surface, thereby introducing functional end groups for tethering to ligands.

In the preferred embodiment, the surface is modified to insert amphiphilic polymers or surfactants that match the polymer phase HLB or hydrophile-lipophile balance, as demonstrated in the following example. HLBs range from 1 to 15. Surfactants with a low HLB are more lipid loving and thus tend to make a water in oil emulsion while those with a high HLB are more hydrophilic and tend to make an oil in water emulsion. Fatty acids and lipids have a low HLB below 10. After conjugation with target group (such as hydrophilic avidin), HLB increases above 10. This conjugate is used in emulsion preparation. Any amphiphilic polymer with an HLB in the range 1-10, more preferably between 1 and 6, most preferably between 1 and up to 5, can be used. This includes all lipids, fatty acids and detergents.

One useful protocol involves the "activation" of hydroxyl groups on polymer chains with the agent, carbonyldiimidazole (CDI) in aprotic solvents such as DMSO, acetone, or THF. CDI forms an imidazolyl carbamate complex with the hydroxyl group which may be displaced by binding the free amino group of a ligand such as a protein. The reaction is an N-nucleophilic substitution and results in a stable N-alkylcarbamate linkage of the ligand to the polymer. The "coupling" of the ligand to the "activated" polymer matrix is maximal in the pH range of 9-10 and normally requires at least 24 hrs. The resulting ligand-polymer complex is stable and resists hydrolysis for extended periods of time.

Another coupling method involves the use of 1-ethyl-3-(3-dimethylaminopropyl) carbodiimide (EDAC) or "water-soluble CDT" in conjunction with N-hydroxylsulfosuccinimide (sulfo NHS) to couple the exposed carboxylic groups of polymers to the free amino groups of ligands in a totally aqueous environment at the physiological pH of 7.0. Briefly, EDAC and sulfo-NHS form an activated ester with the carboxylic acid groups of the polymer which react with the amine end of a ligand to form a peptide bond. The resulting peptide bond is resistant to hydrolysis. The use of sulfo-NHS in the reaction increases the efficiency of the EDAC coupling by a factor of ten-fold and provides for exceptionally gentle conditions that ensure the viability of the ligand-polymer complex.

By using either of these protocols it is possible to "activate" almost all polymers containing either hydroxyl or carboxyl groups in a suitable solvent system that will not dissolve the polymer matrix.

A useful coupling procedure for attaching ligands with free hydroxyl and carboxyl groups to polymers involves the use of the cross-linking agent, divinylsulfone. This method would be useful for attaching sugars or other hydroxylic compounds with bioadhesive properties to hydroxylic matrices. Briefly, the activation involves the reaction of divinylsulfone to the hydroxyl groups of the polymer, forming the vinylsulfonyl ethyl ether of the polymer. The vinyl groups will couple to alcohols, phenols and even amines. Activation and coupling take place at pH 11. The linkage is stable in the pH range from 1-8 and is suitable for transit through the intestine.

Any suitable coupling method known to those skilled in the art for the coupling of ligands and polymers with double bonds, including the use of UV crosslinking, may be used for attachment of molecules to the polymer.

Coupling is preferably by covalent binding but it may also be indirect, for example, through a linker bound to the polymer or through an interaction between two molecules such as strepavidin and biotin. It may also be by electrostatic attraction by dip-coating.

The molecules to be delivered can also be encapsulated into the polymer using double emulsion solvent evaporation techniques, such as that described by Luo et al., Controlled DNA delivery system, Phar. Res., 16: 1300-1308 (1999).

IV. Methods of Use

The nanoparticles disclosed herein are generally useful for intracellular delivery of inhibitory RNAs in a controlled and sustained manner. Complexation of inhibitory RNAs with polycations allows for a significantly enhanced encapsulation efficiency of the inhibitory RNAs into polymeric nanoparticles when compared to the encapsulation efficiency of inhibitory RNAs in the absence of polycations. The nanoparticulate size of the polymeric particles disclosed herein provides for greater internalization of the particles by cells when compared with microparticulate polymeric particles. Efficient internalization of polymeric particles containing inhibitory RNAs complexed to a polycation is critical for achieving significant reductions in gene expression in cells and tissues. Inhibitory RNA/polycation complexes that are released from polymeric particles outside of cells are not efficiently internalized by cells. The examples below demonstrate that siRNA/polycation complexes exposed to cells in the absence of nanoparticle carriers required transfection agents to be efficiently transported into cells. The polymeric nanoparticles disclosed herein also achieve greater penetration into tissues in vivo as compared with microparticles. Encapsulation of inhibitory RNA/polycation complexes by polymeric nanoparticles allows for the controlled and sustained release of inhibitory RNAs over a period of time. As discussed above, the release rates of encapsulated inhibitory RNAs from the particles can be varied through the selection of the polymers used to form the nanoparticles, and the technique used to form the nanoparticles.

The advantageous properties of the nanoparticles disclosed herein, including: 1) high encapsulation efficiency of inhibitory RNAs into nanoparticles provided by complexing to polycations, 2) small size of the nanoparticles that increases cell internalization of the nanoparticles, and 3) sustained release of encapsulated inhibitory RNAs by the nanoparticles, allows for administration of an effective amount of inhibitory RNAs to cells or tissues over an extended period of time. As defined herein, an "effective amount" of an inhibitory RNA refers to an amount of inhibitory RNA sufficient to cause a reduction of at least 10%, more preferably, 20%, 30%, 40%, 50%, 60%, 70%, 75%, 80%, 85%, 90%, 95%, or more of the expression of the mRNA that is targeted by the inhibitory RNA. In one embodiment, the nanoparticles release an effective amount of inhibitory RNA over a period of at least a week. In another embodiment, the nanoparticles release an effective amount of inhibitory RNA over a period of at least two weeks. In another embodiment, the nanoparticles release an effective amount of inhibitory RNA over a period of at least one month.

A. Subjects to be Treated

The nanoparticles disclosed herein are generally useful for administering inhibitory RNAs to a subject for the treatment or inhibition of a disease or disorder. Treatment may be prophylactic or therapeutic. Diseases or disorders that can be treated or inhibited using the inhibitory RNA-containing polymeric nanoparticles disclosed herein include any disease or disorder in which it is desirable to reduce the expression of one or more target mRNAs.

mRNAs to be targeted by inhibitory RNAs encapsulated in polymeric nanoparticles can be an mRNAs that are expressed by genes that are endogenous to the cells of the subject being treated, or can be derived from genes that are contained within the genome that is exogenous to the subject being treated, such as a viral genome. Exemplary diseases and disorders that can be treated or inhibited using the nanoparticles disclosed herein include, but are not limited to, cancer, diseases and disorders that result from viral infections, inflammatory and autoimmune diseases and disorders, graft rejection and graft-versus-host disease. mRNAs that are aberrantly expressed in these conditions are well known in the art. Any mRNA known to be aberrantly expressed in the condition to be treated can be targeted by siRNA encapsulated with the nanoparticles disclose herein. In a preferred embodiment, the mRNA that is targeted by the encapsulated inhibitory RNA is an mRNA that encodes a protein that is known to function in the initiation or progression of the disease or disorder that is to be treated or inhibited.

i. Subjects with or at Risk of Developing Malignant Tumors

In a mature animal, a balance usually is maintained between cell renewal and cell death in most organs and tissues. The various types of mature cells in the body have a given life span; as these cells die, new cells are generated by the proliferation and differentiation of various types of stem cells. Under normal circumstances, the production of new cells is so regulated that the numbers of any particular type of cell remain constant. Occasionally, though, cells arise that are no longer responsive to normal growth-control mechanisms. These cells give rise to clones of cells that can expand to a considerable size, producing a tumor or neoplasm. A tumor that is not capable of indefinite growth and does not invade the healthy surrounding tissue extensively is benign. A tumor that continues to grow and becomes progressively invasive is malignant. The term cancer refers specifically to a malignant tumor. In addition to uncontrolled growth, malignant tumors exhibit metastasis. In this process, small clusters of cancerous cells dislodge from a tumor, invade the blood or lymphatic vessels, and are carried to other tissues, where they continue to proliferate. In this way a primary tumor at one site can give rise to a secondary tumor at another site. The compositions and method described herein may be useful for treating subjects having malignant tumors.

Malignant tumors which may be treated are classified herein according to the embryonic origin of the tissue from which the tumor is derived. Carcinomas are tumors arising from endodermal or ectodermal tissues such as skin or the epithelial lining of internal organs and glands. A melanoma is a type of carcinoma of the skin for which this invention is particularly useful. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

The types of cancer that can be treated in with the provided compositions and methods include, but are not limited to, the following: bladder, brain, breast, cervical, colo-rectal, esophageal, kidney, liver, lung, nasopharangeal, pancreatic, prostate, skin, stomach, uterine, and the like. Administration is not limited to the treatment of an existing tumor or infectious disease but can also be used to prevent or lower the risk of developing such diseases in an individual, i.e., for prophylactic use. Potential candidates for prophylactic vaccination include individuals with a high risk of developing cancer, i.e., with a personal or familial history of certain types of cancer.

ii. Subjects Infected with or Exposed to Infectious Agents

Subjects with or exposed to infectious agents can be treated therapeutically or prophylactically with inhibitory RNA nanoparticle compositions disclosed herein. Infectious agents include bacteria, viruses and parasites. In some instances, the subject can be treated prophylactically, such as when there may be a risk of developing disease from an infectious agent. An individual traveling to or living in an area of endemic infectious disease may be considered to be at risk and a candidate for prophylactic vaccination against the particular infectious agent. Preventative treatment can be applied to any number of diseases where there is a known relationship between the particular disease and a particular risk factor, such as geographical location or work environment.

iii. Subjects with or at Risk of Developing Autoimmune Diseases or Disorders

The compositions and methods are useful for the treatment or prevention of autoimmune diseases and disorders. Exemplary autoimmune diseases include vasculitis, Wegener's granulomatosis, Addison's disease, alopecia, ankylosing spondylitis, antiphospholipid syndrome, Behcet's disease, celiac disease, chronic fatigue syndrome, Crohn's disease, ulcerative colitis, type I diabetes, fibromyalgia, autoimmune gastritis, Goodpasture syndrome, Graves' disease, idiopathic thrombocytopenic purpura (ITP), lupus, Meniere's multiple sclerosis, myasthenia gravis, pemphigus vulgaris, primary biliary cirrhosis, psoriasis, rheumatoid arthritis, rheumatic fever, sarcoidosis, scleroderma, vitiligo, vasculitis, small vessel vasculitis, hepatitis, primary biliary cirrhosis, rheumatoid arthritis, Chrohn's disease, ulcerative colitis, sarcoidosis, scleroderma, graft versus host disease (acute and chronic), aplastic anemia, and cyclic neutropenia.

iv. Subjects Undergoing or at Risk of Graft Rejection or Graft-Versus-Host Disease The compositions and methods are useful for the treatment or prevention of graft rejection or graft versus host disease. The methods and compositions can be used in the prevention or treatment of any type of allograft rejection or graft versus host disease for any type of graft, including a xenograft. The allograft can be an organ transplant, such as, but not limited to, a heart, kidney, liver, lung or pancreas. Alternatively, the allograft can be a tissue transplant, such as, but not limited to, heart valve, endothelial, cornea, eye lens or bone marrow tissue transplant. In yet other embodiments, the allograft can be a skin graft.

B. Combination Therapies

The disclosed nanoparticle compositions can be administered alone or in combination with one or more additional therapeutic agents. For example, administration of inhibitory RNA-containing polymeric nanoparticles to treat or inhibit cancer may be coupled with surgical, chemotherapeutic, radiologic, hormonal and other immunologic approaches in order to affect treatment.

For example, the disclosed nanoparticles can be administered with an antibody or antigen binding fragment thereof specific for a growth factor receptors or tumor specific antigens. Representative growth factors receptors include, but are not limited to, epidermal growth factor receptor (EGFR; HER1); c-erbB2 (HER2); c-erbB3 (HER3); c-erbB4 (HER4); insulin receptor; insulin-like growth factor receptor 1 (IGF-1R); insulin-like growth factor receptor 2/Mannose-6-phosphate receptor (IGF-II R/M-6-P receptor); insulin receptor related kinase (IRRK); platelet-derived growth factor receptor (PDGFR); colony-stimulating factor-1 receptor (CSF-1R) (c-Fms); steel receptor (c-Kit); Flk2/Flt3; fibroblast growth factor receptor 1 (Flg/Cek1); fibroblast growth factor receptor 2 (Bek/Cek3/K-Sam); Fibroblast growth factor receptor 3; Fibroblast growth factor eceptor 4; nerve growth factor receptor (NGFR) (TrkA); BDNF receptor (TrkB); NT-3-receptor (TrkC); vascular endothelial growth factor receptor 1 (Flt1); vascular endothelial growth factor receptor 2/Flk1/KDR; hepatocyte growth factor receptor (HGF-R/Met); Eph; Eck; Eek; Cek4/Mek4/HEK; Cek5; Elk/Cek6; Cek7; Sek/Cek8; Cek9; Cek10; HEK11; 9 Ror1; Ror2; Ret; Axl; RYK; DDR; and Tie.

Additional therapeutic agents include conventional cancer therapeutics such as chemotherapeutic agents, cytokines, chemokines, and radiation therapy. The majority of chemotherapeutic drugs can be divided into: alkylating agents, antimetabolites, anthracyclines, plant alkaloids, topoisomerase inhibitors, and other antitumour agents. All of these drugs affect cell division or DNA synthesis and function in some way. Additional therapeutics include monoclonal antibodies and the new tyrosine kinase inhibitors e.g. imatinib mesylate (GLEEVEC® or GLIVEC®), which directly targets a molecular abnormality in certain types of cancer (chronic myelogenous leukemia, gastrointestinal stromal tumors).

Representative chemotherapeutic agents include, but are not limited to, cisplatin, carboplatin, oxaliplatin, mechlorethamine, cyclophosphamide, chlorambucil, vincristine, vinblastine, vinorelbine, vindesine, taxol and derivatives thereof, irinotecan, topotecan, amsacrine, etoposide, etoposide phosphate, teniposide, epipodophyllotoxins, trastuzumab (HERCEPTIN®), cetuximab, and rituximab (RITUXAN® or MABTHERA®), bevacizumab (AVASTIN®), and combinations thereof.

C. Methods of Administration

In general, methods of administering nanoparticles are well known in the art. Any acceptable method known to one of ordinary skill in the art may be used to administer the nanoparticles disclosed herein to a subject. The administration may be localized (i.e., to a particular region, physiological system, tissue, organ, or cell type) or systemic. Nanoparticles can be administered by a number of routes including, but not limited to: oral, inhalation (nasal or pulmonary), intravenous, intraperitoneal, intramuscular, transdermal, subcutaneous, topical, sublingual, or rectal means. Injections can be e.g., intravenous, intradermal, subcutaneous, intramuscular, or intraperitoneal. In some embodiments, the injections can be given at multiple locations.

The nanoparticles disclosed herein are particularly useful for topical administration. Delivery of inhibitory RNAs such as siRNA to mucosal tissue like the lungs and vagina appears to be extremely efficient and has been shown to occur even in the absence of transfection agents (Bitko, et al., Nat. Med., 11(1):50-5 (2005); Peer, et al., Science, 319(5863):627-30 (2008)). The examples below demonstrate that siRNA-loaded poly(lactide-co-glycolide) (PLGA) nanoparticles administered to the mucosal surface of the mouse female reproductive tract produce efficient gene silencing throughout the reproductive tract compared to lipoplex delivery. This approach might lead directly to clinical approaches for delivery of inhibitory RNAs to treat infectious disease or cancer, prevent sexually transmitted diseases, or regulate fertility.

Administration of nanoparticle formulations may be accomplished by any acceptable method which allows an effective amount of the nanoparticles to reach its target. The particular mode selected will depend upon factors such as the particular formulation, the severity of the state of the subject being treated, and the dosage required to induce an effective response.

Unless defined otherwise, all technical and scientific terms used herein have the same meanings as commonly understood by one of skill in the art to which the disclosed invention belongs.

EXAMPLES

Example 1

Encapsulation of siRNAs into Nanoparticles

Materials and Methods:

siRNAs. siRNAs were synthesized using 2'-O-ACE-RNA phosphoramidites (A4 grade, Dharmacon Research). siRNAs sequences directed against erk2 and EGFP were as previously described (Novina, et al., Nat. Med., 8:681-6 (2002); Sun, et al., Am. J. Physiol. Regul. Integr. Comp. Physiol., 293(3): R1239-46 (2007)). The sense and anti-sense strands of siRNAs used in these studies are listed in Table 1.

TABLE 1

Sequence and properties of siRNAs

| Name | Sequence[a] (5'→3') | GC-content (%) | Bases (nt) | Target |
|---|---|---|---|---|
| deoMMC | d(GGCUACGUCCAGGAGCGCACC) (SEQ ID NO: 1) | 71 | 21 | siRNA mimic |
| siERK2 | r(UGCUGACUCCAAAGCUCUG)d(TT) (SEQ ID NO: 2) | 48 | 21 | Mitogen-activated protein kinase 1 |
| siEGFP | r(GGCUACGUCCAGGAGCGCACC) (SEQ ID NO: 3) | 71 | 21 | Enhanced green fluorescent protein |

[a]Sequence indicates use of deoxyribonucleotides (d) or ribonucleotides (r).

Preparation of siRNA Nanoparticles. Polyamine Complexes with siRNA were formed at room temperature for 15 min on a rotary shaker. The siRNA (25 moles) was combined with the polyamine at a molar ratio of the polyamine nitrogen to the polynucleotide phosphate (NIP ratio) of 8:1 or 15:1. The volume of spermidine (Sigma) or putrescine (Sigma) used to obtain these ratios were determined as follows (Grayson, et al., *Pharmaceut. Res.*, 23:1868-76 (2006)):

$$V_{NH2} = \frac{C_{siRNA,final} \times M_{w,siRNA} / C_{siRNA,final} \times M_{w,P} \times \Phi_{N:P} \times \Phi V_{final}}{C_{NH2} / M_{w,NH2}}$$

$M_{w,siRNA}$=molecular weight of siRNA duplex, $M_{w,P}$=molecular weight of phosphate group of siRNA, $\Phi_{N:P}$=N:P ratio (molar ratio of nitrogens from polyamine to the ratio of phosphates from the siRNA), $C_{NH2}$, stock=concentration of polyamine stock solution, and $M_{w,NH2}$=molecular weight per nitrogen of polyamine. PLGA nanoparticles loaded with naked siRNA (uncomplexed) or the siRNA/polyamines were formulated by a double-emulsion solvent evaporation technique (Fahmy, et al., *Biomaterials*, 26:5727-36 (2005)). In brief, siRNA were reconstituted in deionized water in the absence or presence of complexing agents. This aqueous solution was then added dropwise to a polymer solution of PLGA (200 mg, 50:50, Polysciences and Birmingham) dissolved in dichloromethane (2 mL) to form the first emulsion. This mixture was then added dropwise to 4 mL of 5% polyvinyl alcohol (PVA) and sonicated to form the double emulsion. The final emulsion was poured into a beaker containing aqueous 0.3% (v/v) PVA and stirred for 3 hours to allow the dichloromethane to evaporate and the particles to harden. The concentration of PVA used to form the emulsion, and the sonication time and amplitude have been optimized for formulating particles with a diameter of 0.1 to 300 μm. Particles are collected by centrifugation, washed, rapidly frozen, and lyophilized.

Characterization of nanoparticle size, and siRNA loading and encapsulation efficiency. To determine loading and encapsulation efficiency, 10-20 mg of siRNA nanoparticles were dissolved in 0.5 mL or dichloromethane at room temperature for 30 min. The siRNA was extracted from the organic phase using two volumes each of 0.5 mL TE buffer (10 mM Tris-HCl, 1 mM EDTA, pH 7.4). The TE buffer was added to the organic phase and vortexed vigorously for 1 min, and then centrifuged at 12,000 rpm for 5 min at 4° C. The combined 1 mL aqueous fraction was analyzed for double-stranded RNA content using the QuantIT™ PicoGreen™ assay according the manufacturer's instructions (Invitrogen). A standard curve correlating fluorescence and siRNA concentration was used to determine the amount of siRNA loaded into the PLGA particles. The efficiency of the extraction procedure was assessed by extracting a known amount of siRNA. Following fluorescence quantification, the siRNA were precipitated from the aqueous fraction by addition of 0.3 M sodium acetate and 70% (v/v) ethanol. This solution was incubated at −20° C. for 30 min, and then centrifuged at 12,000 rpm and 4° C. for 30 min to collect the precipitate. The pellet was dried and analyzed on a 3% (w/v) agarose gel. Particles size and surface charge were determined by static light scattering (DLS) using a ZetaPals (Brookhaven Instruments) ζ-potential and particle size analyzer. Particle formulations were analyzed in triplicate at a concentration of 10 μg/mL in a total volume of 2 mL in various solvents. The average values from a total of 5-10 runs of 30 seconds each were used to determine both values. Particle size was also analyzed by image analysis of micrographs obtained by scanning electron microscopy (SEM). The samples were coated with 25 nm-thick gold using a quick carbon coater. The particle diameter and size distribution of the microspheres were determined by image analysis of >1,000 particles using image analysis software (ImageJ, National Institute of Health). These micrographs were also used to assess particle morphology.

Results:

An siRNA mimic was used to develop methods for formulating and characterizing siRNA loaded PLGA nanoparticles. This mimic preserves the GC-content, molecular weight, and charge density of siRNA but uses deoxynucleotides for increased stability. The mimic was formed by annealing two DNA oligonucleotides to form a double-stranded product, deoMMC (Table 1). This mimic was used to test the hypothesis that loading and encapsulation efficiency of deoMMC can be improved by complexing with polyamines. Gel-shift assays were used to determine the optimal ratio to combine the mimic and polyamines, and then various deoMMC nanoparticles were formulated using a double-emulsion solvent evaporation technique (Fahmy, et al., *Biomaterials*, 26:5727-36 (2005)). All nanoparticles exhibited a similar size, morphology, and surface charge. The encapsulation efficiency of the naked mimic was less than 5% but increased to 20-40% when the mimic was complexed with spermidine or putrescine (FIG. 1), which are natural polyamines known to interact and stabilize nucleic acids in vivo (Bachrach, et al., *Curr. Protein Pept. Sci.*, 6(6):559-66 (2005); Childs, et al., *Cell. Mol. Life. Sci.*, 60(7):1394-406 (2003)).

Based on the experience with the mimic, spermidine (Spe) was selected as a counterion for encapsulating a siRNA targeted against the erk2 gene (siERK2) encoding for a protein kinase, MAPK1 (Table 1). Spermidine was combined with siERK2 at a molar ratio of the polyamine nitrogen to nucleic acid phosphate of 8:1 (N:P ratio) (Grayson, et al., *Pharm. Res.*, 23(8):1868-76 (2006)). An encapsulation efficiency of 40% was obtained, and a loading of 50 pmoles/mg PLGA, which equates to several hundred molecules of siRNA per nanoparticle (Table 2).

TABLE 2

Properties of PLGA nanoparticles loaded with siRNA

| Formulation | Size[a] (nm) | ζ-potential[b] (mV) | Loading (pmoles/mg PLGA) | Encapsulation Efficiency (%) | siRNA molecules per particle |
|---|---|---|---|---|---|
| siERK2/Spe | 198 ± 54 | −34 ± −3 | 65 ± 12 | 56 ± 10 | 225 |
| siEGFP/Spe | 183 ± 61 | −29 ± −2 | 27 ± 2 | 21 ± 1 | 81 |

[a]Mean particle diameter was determined by ImageJ (NIH) analysis of SEM micrographs. The mean diameter determined by static light scattering for siERK2/Spe and siEGFP/Spe nanoparticles was 359 nm and 348 nm, respectively (ZetaPals, Brookaven Instruments).
[b]Nanoparticles were analyzed in triplicate at a concentration of 10 μg/mL in a total volume of 2 mL. Conductance of deionized (DI) water is 3.8 ± 1.0 μS.

Example 2 siRNA Nanoparticle Efficacy in Cultured Cells

Materials and Methods:

Cell lines. HepG2 hepatocytes (courtesy of Yale Liver Center) were maintained in Eagle's minimum essential medium (E-MEM, ATCC) supplemented with 10% (v/v) fetal bovine serum (FBS, Sigma) and 1% (v/v) penicillin/streptomycin (Sigma). NIH/3T3 fibroblast were maintained in Dulbecco's Modified Eagle's Medium with high glucose (DMEM/High) supplemented with 10% (v/v) PBS and 1% (v/v) penicillin/streptomycin. HeLa cells were maintained in RPMI-1640 supplemented with 10% (v/v) FBS and 1% (v/v) penicillin/streptomycin.

In vitro controlled release. Nanoparticles (10-15 mg) were suspended in 1.0 mL of phosphate buffer (pH 7.4), and incubated at 37° C. with gentle shaking (70 rpm). Release of siRNA was monitored at several time intervals over 30 days. At each sampling time, the nanoparticle suspension was centrifuged for 5 min at 14,000 rpm. The supernatant (0.5 mL) was removed for quantification of fluorescence and an equivolume of PBS was replaced for continued monitoring of siRNA release. The amount of residual siRNA in nanoparticles was determined using the same analytical method of encapsulation efficiency.

Nanoparticle delivery to cultured cells. Nanoparticles encapsulating siRNA were compared against control nanoparticles encapsulating only the polyamine or dsMMC/polyamine complexes in cultured HepG2 hepatocytes, NIH/3T3 fibroblasts, and HeLa cells. Nanoparticles were resuspended in the appropriate cell media at 0.5 mg/mL (10 nM siRNA) or 1 mg/mL (20 nM siRNA) polymer. Cells were seeded in T25 flasks and treated with the nanoparticle preparations when the cells reached 30-50% confluency. Cells were analyzed for gene expression 3 d after nanoparticle treatment. For the time course experiments, HeLa cells were seeded at different levels of confluency depending on when the cells were being analyzed for gene expression: 1 d=80%, 3 d=50%, 5-14 d=10%. For the longer time points (5-14 d), cells were passaged when they became 90% confluent and then resuspended in fresh media containing the nanoparticle suspension that was collected by centrifugation.

Quantitative RT-PCR. Total RNA (1 μg) was isolated using a RNeasy® Mini Kit (Qiagen) according to the manufacturer's protocol. Purified total mRNA was reverse transcribed using the iScript™ cDNA Synthesis kit (Biorad) to generate cDNA. Real-time PCR was performed on 2 μL of cDNA combined with the iQ SyBr™ Green (Biorad) reagents for fluorescent detection of PCR products. AU reactions were performed in a 20 μL volume in duplicate. Primers used for RT-PCR were:

```
                                       (SEQ ID NO: 4)
Hu-erk2_forward:  5'-CCGTGACCTCAAGCCTTC-3'

(SEQ ID NO: 5)
Hu-erk2_reverse:  5'-GCCAGGCCAAAGTCACAG-3'

(SEQ ID NO: 6)
Mu-erk2_forward:  5'-CGTTCTGCACCGTGACCT-3'

(SEQ ID NO: 7)
Mu-erk2_reverse:  5'-ATCTGCAACACGGGCAAG-3'

(SEQ ID NO: 8)
GAPDH_forward:    5'-TTCACCACCATGGAGAAGGC-3'

(SEQ ID NO: 9)
GAPDH_reverse:    5'-GGCATGGACTGTGGTCATGA-3'
```

PCR parameters consisted of 5 min activation of the DNA polymerase at 95° C., followed by 40 cycles of 95° C.×20 s, 60° C.×30 s, and 72° C.×20 s. Messenger RNA expression was normalized to the expression of glyceraldehyde 3-phosphate dehydrogenase (GAPDH). Primer specificity was verified by melt curve analysis and agarose gel electrophoresis.

Results:

Encapsulation of siERK2 did not alter its physicochemical or functional properties: siERK2/Spe extracted from the nanoparticles was as efficient as a positive control in silencing MAPK1 expression in cultured cells. Gel electrophoresis identified that the charge and molecular weight of siMAPK1 extracted from PLGA nanoparticles was similar to the control stock siRNA reagent and protein immunoblotting showed that siMAPK1 extracted from PLGA nanoparticles silences gene expression in cultured HepG2 hepatocytes and HeLa cells. The extracted siERK2/Spe required a transfection agent to direct gene silencing, suggesting that siERK2/Spe alone is inefficiently transported intracellularly and therefore unable to enter the RNAi pathway.

Figure 2:
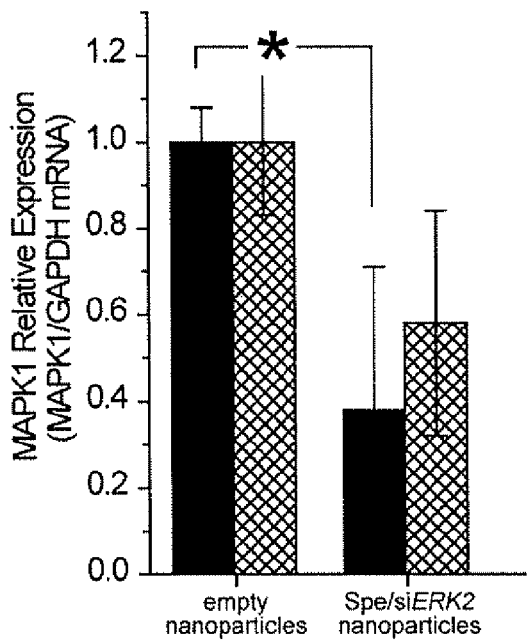
FIG. 2 is a bar graph showing the effect of nanoparticles containing siMAPK1 on MAPK1 expression in cultured cells. Either empty nanoparticles or nanoparticles encapsulating an siRNA targeted against erk2 were administered to cultured HepG2 hepatocytes (solid bars) and 3T3NIH fibroblasts (hatched bars). Nanoparticles were present in the appropriate cell media at a concentration of 0.5 mg/mL polymer (10 nM siRNA). Bars represent the mean±s.d. (n=3); *=p≤0.05.
Figure 3:
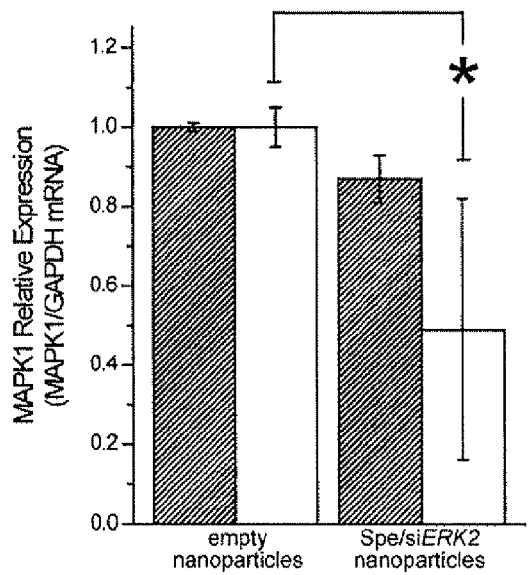
FIG. 3 is a bar graph showing the dose-dependency of the effect of nanoparticles delivering siERK2 on MAPK1 expression in cultured cells. Cultured HeLa cells were administered 0.5 mg/mL (hatched bars) or 1.0 mg/mL (open bars) nanoparticles encapsulating a siRNA targeted against erk2. Bars represent the mean±s.d. (n=3); *=p≤0.05.
Figure 4:
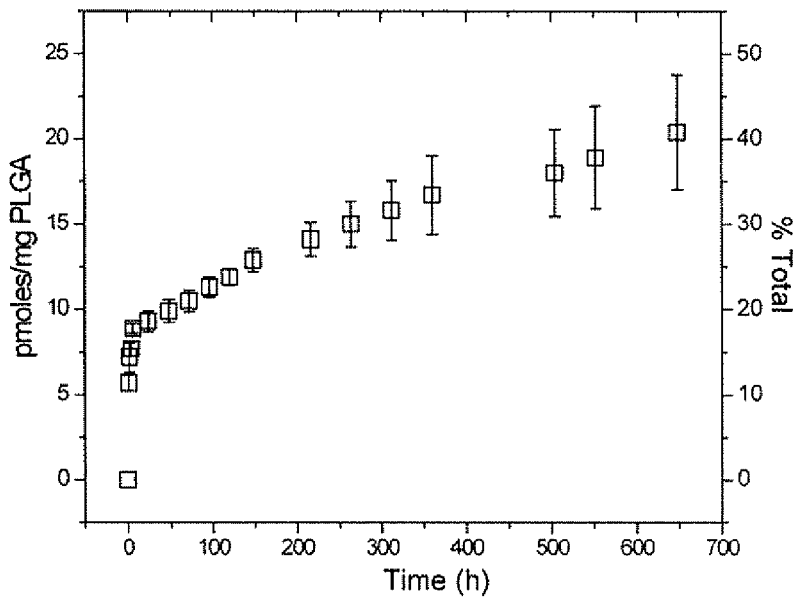
FIG. 4 is a line graph showing in vitro release of siERK2 from PLGA nanoparticles (pmoles/mg PLGA over time in hours). Nanoparticles (10-15 mg) were suspended in 1.0 ml of phosphate buffer (pH 7.4), and incubated at 37° C. with gentle shaking (70 rpm). Cumulative release of siERK2/Spe from nanoparticles was measured for about 30 days. Values represent the mean±s.d.
Figure 5:
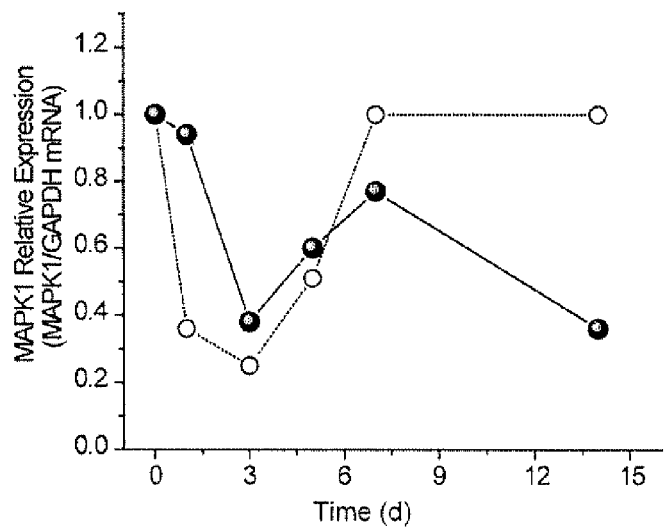
FIG. 5 is a line graph showing the effect of nanoparticles delivering siMAPK1 on MAPK1 expression in cultured cells as a function of time in days. HepG2 cells were cultured in the presence of siMAPK1 nanoparticles (closed circles) or siMAPK1 complexed with a commercial transfection reagent (open circles) and MAPK1 expression was measured over a 14 day period.

To test the delivery of siRNA via nanoparticles, siERK2/Spe nanoparticles (0.5 mg/mL, approximately 10 nM siERK2) were administered to cultured cells and observed targeted gene knockdown in NIH/3T3 fibroblasts and HepG2 hepatocytes (FIG. 2). Knockdown of MAPK1 expression in HeLa cells was observed only after doubling the nanoparticle concentration in suspension, which suggests that knockdown efficiency with siRNA nanoparticles is dose and cell dependent (FIG. 3). These biodegradable nanoparticles loaded with siRNA were then evaluated for their ability to prolong the gene silencing effect. In vitro controlled release profiles for siERK2/Spe nanoparticles show a modest burst release after the first day followed by sustained linear release of 0.4 pmoles/mg·day (FIG. 4). Even after 30 days, less than 50% of the encapsulated siERK2 had been released. These sustained release profiles translated to prolonged gene silencing in HepG2 cell cultures, where it was observed that siERK2/Spe nanoparticles produced significant and sustained gene silencing compared to a commercial transfection agent (FIG. 5). Gene silencing is sustained for at least 14 days in HepG2 cells cultured with siMAPK1 nanoparticles whereas total recovery of MAPK1 expression was seen after 7 days when using a commercial transfection agent to deliver siMAPK1.

Example 3 siRNA Nanoparticle Efficacy In Vivo

Materials and Methods:

EVAc Disc. Poly Ethylene vinyl acetate ("EVAc") discs were prepared by solvent evaporation as described by Luo, et al., *Pharm. Res.*, 16(8):1300-8 (1999); Shen, et al., *J. Control. Release*, 86(2-3):339-48 (2003). Prior to encapsulation, siRNA was complexed with RNAiMax (Invitrogen). Equal volumes of siRNA (80 μM in OptiMEM) and RNAiMax (diluted 4 parts reagent and 1 part OptiMEM or 800 μL/mL) were combined and incubated at room temperature for 20 minutes. A 20% (wt/vol) Ficoll 70 (Sigma) in OptiMEM was added for a final concentration of 30 μM siRNA complexes and 5% (wt/vol) Ficoll 70. The mixture was flash frozen and lyophilized for 48 hours. The dried mixture of sugar and complexes was ground to a fine powder. The powder was added to poly(ethylene-co-vinyl acetate) dissolved in methylene chloride at 10% (w/v), vortexed, and poured into a mold chilled on dry ice. Once polymer/sugar/complexes matrix set, it was transferred to −20° C. for 2 days. Matrix was placed under vacuum for another 2 days to remove all traces of methylene chloride. The matrix was cut into small discs for implantation (approximately 1.0 mm in thickness, 2.5 mm in diameter) with a cork borer. The sugar/complex powder comprised 40% (wt/wt) of the disc and the effective dose of complex siRNA per disc was between 750-1000 pg.

Intravaginal EVAc implantation and lavage. Female FVB.Cg-Tg(GFPU)5Nagy mice (6-8 weeks old) were obtained from Jackson Laboratories. Mice were subcutaneously injected with 2 mg Depo-Provera (medroxyprogesterone acetate, Pfizer), and 5 days later treated with different siRNA delivery vehicles. EVAc disks were implanted by a simple surgical procedure (Radomsky, et al., *Biol. Reprod.*, 47(1):133-40 (1992); Wyatt, et al., *J. Control. Release*, 50(1-3):93-102 (1998)): an incision in the abdominal wall exposed the peritoneum providing access to the reproductive tract, the disc was inserted intravaginally, and sutured to the vaginal wall slightly past the cervix. After implantation in the reproductive tract the incisions were closed. Lipoplexes (500 pmoles) was complexed with RNAiMax (Invitrogen) according to the manufacturer's protocol and then administered intravaginally in a volume of 12 μL. Nanoparticles (1 mg, 30 pmoles) were resuspended in PBS (12 μL) and administered intravaginally every day for 3 days. Animals were sacrificed and the reproductive tract was analyzed for EGPF expression 3 d after from the start of treatment. Six treatment groups were tested, containing three animals each: nanoparticles with and without siRNA, EVAc vaginal rings with and without siRNA, and lipoplexes with and without siRNA.

Tissue sections and microscopy. For fluorescence microscopy, dissected tissue was placed in optimal cutting temperature compound (TissueTek) and snap-frozen in liquid nitrogen. Microscopy images were collected on 9 μM tissue sections using an Olympus IX71 inverted fluorescent microscope. Image fluorescence was quantified using image analysis software (ImageJ).

Statistical analysis. All data were analyzed by a Student's t-test to determine statistical significance.

Figure 6:
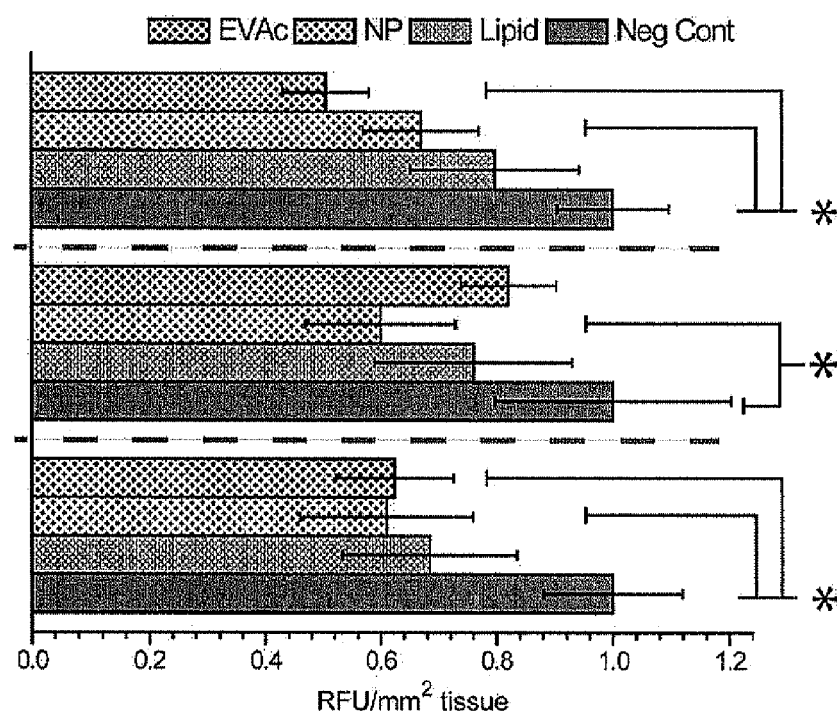
FIG. 6 is a bar graph showing the effect of intravaginal siRNA administration using various siRNA delivery vehicles on gene expression in the reproductive tract of female EGFP mice. An siRNA targeted against EGFP was formulated into nanoparticles, ethylene vinyl acetate (EVAc) vaginal rings, or lipoplexes using a commercial transfection reagent. siRNA nanoparticles and lipoplexes were delivered by lavage into the vaginal tract of EGFP mice whereas vaginal rings were implanted surgically at the crown of the cervix. Animals were sacrificed 3 days after the start of treatment, and the reproductive tract was analyzed for EGFP expression. Images were obtained at 10× magnification and fluorescence images were obtained at 1 second exposure times. Data were quantified for EGFP fluorescence per area of tissue in the three different regions of the reproductive tract. Bars represent the mean±s.d., *p<0.05 (two sample t-test).

Results:

The efficiency of the siRNA nanoparticles to cause gene silencing in vivo was then tested and compared nanoparticles to other delivery methods. An siRNA targeted against EGFP was formulated into biodegradable nanoparticles, non-biodegradable ethylene vinyl acetate (EVAc) vaginal rings, and lipoplexes using a commercial transfection reagent. The nanoparticles and lipoplexes were delivered by lavage into the vaginal tract whereas vaginal rings were implanted surgically at the crown of the cervix in female EGFP transgenic mice (Radomsky, et al., *Biol. Reprod.*, 47(1):133-40 (1992)). In all cases, delivery of siEGFP led to a reduction in EGFP expression throughout the regions of the reproductive tract that we examined: vaginal tract, cervix, and uterine horns. Significant knockdown of EGFP expression was seen only with the polymer delivery systems but not with lipoplexes (FIG. 6). Lipoplexes decreased EGFP expression by only 20%, except in the vaginal tract where each of the three delivery methods reduced gene expression by 40%. The EVAc disks produced significant EGFP silencing in the vaginal tract and uterine horns, but not near the cervix where the disks were implanted. The data indicates that gene silencing using nanoparticles was as efficient as or better than either controlled release via vaginal rings or lipoplexes. In particular, female mice treated topically with siEGFP nanoparticles led to a 40-50% reduction in EGFP expression throughout the reproductive area despite receiving one-fifth less of the total dose given to the EVAc and lipoplex treatment groups. This result suggests that nanoparticles encapsulating siRNA are internalized by the cells of the reproductive tract, and that siRNA released from the nanoparticles enters the RNAi pathway in the cell cytosol to cause gene silencing. The efficient silencing produced by the siRNA nanoparticles was surprising due to the lower dosing. Many applications using siRNA have administered 1-2.5 mg/kg for effective gene silencing in vivo; other studies of vaginal delivery of siRNA have shown effectiveness at doses as small as about 0.3 mg/kg. The data presented here demonstrate that siRNA nanoparticles efficiently cause gene silencing at a dose of 0.1 mg/kg.

We claim:

1. A composition for intracellular delivery of inhibitory polynucleotides consisting essentially of
    polymeric nanoparticles, and
    inhibitory polynucleotides complexed to a polyamine polycation in a molar ratio of the polycation nitrogen ("N") to the polynucleotide phosphate ("P") of between approximately 8:1 and 15:1,
    wherein the nanoparticles are prepared by first forming the polynucleotide-polycation complex in the absence of the polymer of the nanoparticle and subsequently contacting the polynucleotide-polycation complex with the polymer to form nanoparticles encapsulating the polynucleotide-polycation complex,
    wherein the polynucleotide-polycation complex encapsulated nanoparticles are formed by a double-emulsion technique comprising (i) adding an aqueous solution comprising the polynucleotide-polycation complexes to a polymer solution comprising the polymer dissolved in an organic solvent to form a first emulsion; (ii) adding the first emulsion to a first surfactant solution followed by mixing to form a second emulsion; (iii) adding the second emulsion to a second surfactant solution; and (iv) removing the organic solvent to yield polynucleotide-polycation complex encapsulated nanoparticles.

2. The composition of claim 1, wherein the inhibitory polynucleotide is an inhibitory RNA selected from the group consisting of siRNA, shRNA, miRNA, piRNA, external guide sequences (EGS), and ribozymes.

3. The composition of claim 2, wherein the inhibitory RNA is a double-stranded RNA.

4. The composition of claim 1, wherein the polycation is a polyamine selected from the group consisting of spermine, spermidine, cadaverine and putrescine.

5. The composition of claim 4, wherein the nanoparticles are formed of a polymer having targeting or binding molecules attached thereto or therein.

6. The composition of claim 1, wherein the polymeric nanoparticles are between 50 and 500 nanometers in diameter.

7. The composition of claim 2, wherein the inhibitory RNA targets an mRNA encoded by an oncogene or a viral gene.

8. The composition of claim 1, wherein the polycation increases the encapsulation efficiency of the inhibitory polynucleotide by at least 4-fold as compared to the encapsulation efficiency of inhibitory polynucleotide in the absence of the polycation.

9. The composition of claim 1, wherein the polymer is PLGA.

10. The composition of claim 2, wherein the nanoparticles release an effective amount of inhibitory RNA to cause a reduction of at least 10% of the expression of the mRNA that is targeted by the inhibitory nucleic acid over a period of a week.

11. The composition of claim 1 further comprising functional elements bound to or incorporated into the surface of the nanoparticles,
wherein the functional elements are selected from the group consisting of targeting molecules, protein transduction domains and fusogenic peptides.

12. The composition of claim 11, wherein the functional agents are bound to the nanoparticles by coupling agents.

13. The composition of claim 12, wherein the coupling agents are bound to the functional elements by the non-covalent interaction of affinity tags conjugated to the coupling agents and complementary affinity tags conjugated to the functional elements.

14. A method for increasing the encapsulation efficiency of polynucleotides into polymeric particles comprising contacting inhibitory polynucleotides with a polyamine polycation in a molar ratio of the polycation nitrogen ("N") to the polynucleotide phosphate ("P") of between approximately 8:1 and 15:1 to form a polynucleotide-polycation complex and encapsulating the complex within polymeric nanoparticles,
wherein the nanoparticles are prepared by first forming the polynucleotide-polycation complex in the absence of the polymer of the nanoparticle and subsequently contacting the polynucleotide-polycation complex with the polymer,
wherein the polynucleotide-polycation complex encapsulated nanoparticles are formed by a double-emulsion technique comprising (i) adding an aqueous solution comprising the polynucleotide-polycation complexes to a polymer solution comprising the polymer dissolved in an organic solvent to form a first emulsion; (ii) adding the first emulsion to a first surfactant solution followed by mixing to form a second emulsion; (iii) adding the second emulsion to a second surfactant solution; and (iv) removing the organic solvent to yield polynucleotide-polycation complex encapsulated nanoparticles.

15. The method of claim 14, wherein the polycation is a polyamine selected from the group consisting of spermine, spermidine, cadaverine and putrescine.

16. The method of claim 14, wherein the polyamine is spermidine.

17. A method of reducing the expression of an mRNA in a cell comprising administering the composition of claim 2 to cells or an animal in need thereof.

18. The composition of claim 1, wherein the polymer forming the nanoparticles is a synthetic polymer.

19. The composition of claim 1, wherein the N:P ratio is approximately 8:1.

20. The composition of claim 1, wherein the inhibitory polynucleotide is an siRNA, wherein the polyamine polycation is spermine, spermidine, cadaverine, or putrescine, and wherein the molar ratio of the polycation nitrogen ("N") to the polynucleotide phosphate ("P") is approximately 8:1.

21. The composition of claim 20, wherein the inhibitory RNA inhibits viral infection, cell entry, or life cycle.

22. The composition of claim 1, wherein the polynucleotide-polycation complex is formed in an aqueous solution in the absence of the polymer of the nanoparticle and wherein the aqueous solution comprising the polynucleotide-polycation complex is subsequently contacted with the polymer.

* * * * *

SEQUENCE LISTING

```
<160> NUMBER OF SEQ ID NOS: 12

<210> SEQ ID NO 1
<211> LENGTH: 21
<212> TYPE: RNA
<213> ORGANISM: Artificial Sequence
<220> FEATURE:
<223> OTHER INFORMATION: Synthetic SiRNA

<400> SEQUENCE: 1
ggcuacgucc aggagcgcac c                                              21

<210> SEQ ID NO 2
<211> LENGTH: 19
<212> TYPE: RNA
<213> ORGANISM: Artificial Sequence
<220> FEATURE:
<223> OTHER INFORMATION: Synthetic SiRNA
<220> FEATURE:
<221> NAME/KEY: misc_feature
<222> LOCATION: (1)..(16)
<223> OTHER INFORMATION: ribonunucleotides
<220> FEATURE:
<221> NAME/KEY: misc_feature
<222> LOCATION: (17)..(19)
<223> OTHER INFORMATION: deoxyribonunucleotides

<400> SEQUENCE: 2
```

```
ugcugacucc aaagcucug                                                    19

<210> SEQ ID NO 3
<211> LENGTH: 21
<212> TYPE: RNA
<213> ORGANISM: Artificial Sequence
<220> FEATURE:
<223> OTHER INFORMATION: Synthetic SiRNA
<220> FEATURE:
<221> NAME/KEY: misc_feature
<222> LOCATION: (1)..(21)
<223> OTHER INFORMATION: ribonucleotides

<400> SEQUENCE: 3
ggcuacgucc aggagcgcac c                                                 21

<210> SEQ ID NO 4
<211> LENGTH: 18
<212> TYPE: DNA
<213> ORGANISM: Artificial Sequence
<220> FEATURE:
<223> OTHER INFORMATION: Synthetic forward primer for Hu-erk2

<400> SEQUENCE: 4
ccgtgacctc aagccttc                                                     18

<210> SEQ ID NO 5
<211> LENGTH: 18
<212> TYPE: DNA
<213> ORGANISM: Artificial Sequence
<220> FEATURE:
<223> OTHER INFORMATION: Synthetic reverse primer for Hu-erk2

<400> SEQUENCE: 5
gccaggccaa agtcacag                                                     18

<210> SEQ ID NO 6
<211> LENGTH: 18
<212> TYPE: DNA
<213> ORGANISM: Artificial Sequence
<220> FEATURE:
<223> OTHER INFORMATION: Synthetic forward primer for Mu-erk2

<400> SEQUENCE: 6
cgttctgcac cgtgacct                                                     18

<210> SEQ ID NO 7
<211> LENGTH: 18
<212> TYPE: DNA
<213> ORGANISM: Artificial Sequence
<220> FEATURE:
<223> OTHER INFORMATION: Synthetic reverse primer for Mu-erk2

<400> SEQUENCE: 7
atctgcaaca cgggcaag                                                     18

<210> SEQ ID NO 8
<211> LENGTH: 20
<212> TYPE: DNA
<213> ORGANISM: Artificial Sequence
<220> FEATURE:
<223> OTHER INFORMATION: Synthetic forward primer for GAPDH

<400> SEQUENCE: 8
ttcaccacca tggagaaggc                                                   20
```

```
<210> SEQ ID NO 9
<211> LENGTH: 20
<212> TYPE: DNA
<213> ORGANISM: Artificial Sequence
<220> FEATURE:
<223> OTHER INFORMATION: Synthetic reverse primer for GAPDH

<400> SEQUENCE: 9
ggcatggact gtggtcatga                                           20

<210> SEQ ID NO 10
<211> LENGTH: 11
<212> TYPE: PRT
<213> ORGANISM: Human immunodeficiency virus

<400> SEQUENCE: 10

Tyr Gly Arg Lys Lys Arg Arg Gln Arg Arg Arg
1               5                   10

<210> SEQ ID NO 11
<211> LENGTH: 9
<212> TYPE: PRT
<213> ORGANISM: Human immunodeficiency virus

<400> SEQUENCE: 11

Arg Lys Lys Arg Arg Gln Arg Arg Arg
1               5

<210> SEQ ID NO 12
<211> LENGTH: 16
<212> TYPE: PRT
<213> ORGANISM: Unknown
<220> FEATURE:
<223> OTHER INFORMATION: Protein transduction domain

<400> SEQUENCE: 12

Arg Gln Ile Lys Ile Trp Phe Gln Asn Arg Arg Met Lys Trp Lys Lys
1               5                   10                  15
```